US006906243B2

(12) United States Patent
Kipp et al.

(10) Patent No.: US 6,906,243 B2
(45) Date of Patent: Jun. 14, 2005

(54) PLANT MSH2 SEQUENCES AND METHODS OF USE

(75) Inventors: Peter B. Kipp, Houston, TX (US); Gregory D. May, Ardmore, OK (US); Pramod B. Mahajan, Urbandale, IA (US); Christopher L. Baszczynski, Urbandale, IA (US); Tong Zhu, Chapel Hill, NC (US)

(73) Assignees: Boyce Thompson Institute for Plant Research, Ithaca, NY (US); Pioneer Hi-Bred International, Inc., Des Moines, IA (US)

( * ) Notice: Subject to any disclaimer, the term of this patent is extended or adjusted under 35 U.S.C. 154(b) by 374 days.

(21) Appl. No.: 10/029,065

(22) Filed: Dec. 20, 2001

(65) Prior Publication Data

US 2003/0150024 A1 Aug. 7, 2003

(51) Int. Cl.[7] .............................. A01H 1/00; A01H 5/00; A01H 5/10; C12N 15/29; C12N 15/82
(52) U.S. Cl. .................... 800/298; 435/320.1; 435/419; 536/23.6; 800/278; 800/286
(58) Field of Search ..................... 435/320.1; 536/23.6; 800/279, 285, 286, 298

(56) References Cited

U.S. PATENT DOCUMENTS

2003/0143586 A1 * 7/2003 Chao et al. ..................... 435/6

OTHER PUBLICATIONS

Bowers et al 2000, J. Mol. Biol. 302:327–338.*
Pang et al 1997, Molecular and Cellular Biology 17(8): 4465–4473.*
Bowie et al 1990, Science 247:1306–1310.*
Lazar et al 1988, Mol. Cell. Biol. 8:1247–1252.*
Broun et al 1998, Science 282:1315–1317.*
Colliver et al 1997, Plant Molecular Biology 35:509–522.*
Elomaa et al 1996, Molecular Breeding 2:41–50.*
Andersen et al 2002, J. Mol. Med. 80:770–781.*
Liu et al 2003, Nature Reviews Genetics 4:679–689.*
Culligan and Hays Jun. 2000, The Plant Cell, 12:991–1002.*
Abuin, A., et al., "Genetic Analysis of Mouse Embryonic Stem Cells Bearing *Msh3* and *Msh2* Single and Compound Mutations," *Molecular and Cellular Biology*, Jan. 2000, pp. 149–157, vol. 20(1), American Society for Microbiology, USA.
Ade, J., et al., "Four Mismatch Repair Paralogues Coexist in *Arabidopsis thaliana: AtMSH2, AtMSH3, AtMSH6–1* and *AtMSH6–2,*" *Mol. Gen. Genet.*, 1999, pp. 239–249, vol. 262, Springer–Verlag.
Alani, E., et al., "Genetic and Biochemical Analysis of Msh2p–Msh6p: Role of ATP Hydrolysis and Msh2p–Msh6p Subunit Interactions in Mismatch Base Pair Recognition," *Molecular and Cellular Biology*, May 1997, pp. 2436–2447, vol. 17(5), American Society for Microbiology, USA.

Alani, E., et al., "Interaction Between Mismatch Repair and Genetic Recombination in *Saccharomyces cervisiae,*" *Genetics*, May 1994, pp. 19–39, vol. 137, Genetics Society of America, USA.
Cole–Strauss, A., et al., "Targeted Gene Repair Directed by the Chimeric RNA/DNA Oligonucleotide in a Mammalian Cell–Free Extract," *Nucleic Acids Research*, 1999, pp. 1323–1330, vol. 27(5), Oxford University Press.
Culligan, K., and J. Hays, "Arabidopsis MutS Homologs—AtMSH2, AtMSH3, AtMSH6, and a Novel AtMSH7—Form Three Distinct Protein Heterodimers with Different Specificities for Mismatched DNA," *The Plant Cell*, Jun. 2000, pp. 991–1002, vol. 12, American Society of Plant Physiologists, USA.
Culligan, K., and J. Hays, "DNA Mismatch Repair in Plants: An *Arabidopsis thaliana* Gene That Predicts a Protein Belonging to the MSH2 Subfamily of Eukaryotic MutS Homologs," *Plant Physiol.*, 1997, pp. 833–839, vol. 115.
Culligan, K., et al., "Evolutionary Origin, Diversification and Specialization of Eukaryotic MutS Homolog Mismatch Repair Proteins," *Nucleic Acids Research*, 2000, pp. 463–471, vol. 28, Oxford University Press.
Drotschmann, K., et al., "Mutator Phenotypes of Yeast Strains Heterozygous for Mutations in the *MSH2* Gene," *Proc. Natl. Acad. Sci. USA*, Mar. 1999, pp. 2970–2975, vol. 96.
Hohn, B., and H. Puchta, "Gene Therapy in Plants," *Proc. Natl. Acad. Sci. USA*, Jul. 1999, pp. 8321–8323, vol. 96.
Holmes, J., et al., "Strand–Specific Mismatch Correction in Nuclear Extracts of Human and *Drosophila melanogaster* Cell Lines," *Proc. Natl. Acad. Sci, USA*, Aug. 1990, pp. 5837–5841, vol. 87.
Marsischky, G., et al., "Redundancy of *Saccharomyces cerevisiae MSH3* and *MSH2*–dependent Mismatch Repair," *Genes and Development*, 1996, pp. 407–420, vol. 10(4), Cold Spring Harbor Laboratory Press, USA.

(Continued)

*Primary Examiner*—David H Kruse
(74) *Attorney, Agent, or Firm*—Alston & Bird LLP

(57) ABSTRACT

The invention relates to isolated nucleic acid molecules encoding MutS homologues (MSHs). Such MSH proteins are involved in DNA mismatch-repair processes in organisms. The invention provides isolated nucleic acid molecules comprising MSH2 nucleotide sequences which encode MSH2 proteins and MSH2 nucleotide sequences which encode dominant-negative MSH2 variants. Such MSH2 nucleotide sequences find use in altering mismatch repair, mutation rates and recombination frequencies in both eukaryotic and prokaryotic organisms. The invention also provides isolated nucleic acid molecules comprising MSH2 promoter nucleotide sequences. Such MSH2 promoter nucleotide sequences find use in regulating the expression of genes of interest in plants. Additionally provided are isolated proteins, transformed host cells, and transformed plants, tissues, cells and seeds thereof.

31 Claims, 1 Drawing Sheet

OTHER PUBLICATIONS

Mengiste, T., and J. Paszkowski, "Prospects for the Precise Engineering of Plant Genomes by Homologous Recombination," *Biol. Chem.*, 1999, pp. 749–758, vol. 380, Walter de Gruyter, Berlin.

Modrich, P., and R. Lahue, "Mismatch Repair in Replication Fidelity, Genetic Recombination, and Cancer Biology," *Annu. Rev. Biochem.*, 1996, pp. 101–133, vol. 65, Annual Reviews Inc.

Rayssiguier, C., et al., "The Barrier to Recombination Between *Escherichia coli* and *Salmonella typhimurium* Is Disrupted in Mismatch–Repair Mutants," *Nature*, Nov. 1989, pp. 396–401, vol. 342(6248).

Reenan, R., and R. Kolodner, "Characterization of Insertion Mutations in *Saccharomyces cerevisiae MSH1* and *MSH2* Genes: Evidence for Separate Mitochondrial and Nuclear Functions," *Genetics*, Dec. 1992, pp. 975–985, vol. 132(4), Genetics Society of America, USA.

Rice, M., et al., "Genetic Repair of Mutations in Plant Cell–Free Extracts Directed by Specific Chimeric Oligonucleotides," *Plant Physiology*, Jun. 2000, pp. 427–437, vol. 123, American Society of Plant Physiologists, USA.

Studamire, B., et al., "*Saccharomyces cerevisiae* Msh2p and Msh6p ATPase Activities Are Both Required During Mismatch Repair," Dec. 1998, pp. 7590–7601, vol. 18(12), American Society for Microbiology, USA.

Studamire, B., et al., "Separation–of–Function Mutations in *Saccharomyces cerevisiae MSH2* That Confer Mismatch Repair Defects but Do Not Affect Nonhomologous–Tail Removal During Recombination," *Molecular and Cellular Biology*, Nov. 1999, p. 7558–7567, vol. 19(11), American Society for Microbiology, USA.

Vergunst, A., et al., "VirB/D4–Dependent Protein Translocation from *Agrobacterium* into Plant Cells," *Science* Nov. 2000, pp. 979–982, vol. 290.

Wind, N., et al., "Inactivation of the Mouse *Msh2* Gene Results in Mismatch Repair Deficiency Methylation Tolerance, Hyperrecombination, and Predisposition to Cancer," *Cell*, Jul. 1995, pp. 321–330, vol. 82, Cell Press.

GenBank Report for Accession No. AF109243, Direct Submission on Nov. 24, 1998.

GenBank Report for Accession No. AJ007791, Direct Submission on Jul. 9, 1998.

GenBank Report for Accession No. AJ238785, Direct Submission on May 4, 1999.

GenBank Report for Accession No. AJ245967, Direct Submission on Aug. 20, 1999.

\* cited by examiner

| codon | CCN | CTN | TTN | CTN | ACN | GCN | TCN | |
|---|---|---|---|---|---|---|---|---|
| amino acid | P12 | L16 | F27 | L31 | T48 | A49 | S49 | |
| 5' element | | | | | | | | designation |
| class I | CCC | CTG | TTC | CTG | ACA | | TCT | NtMSH2A1 |
| class II | CCT | CTT | TTT | CTA | ACT | GCT | | NtMSH2B1 |
| class II | CCC | CTG | TTC | CTG | ACA | | TCT | NtMSH2A2 |
| class II | CCT | CTT | TTT | CTA | ACT | | TCT | NtMSH2A3 |

FIGURE 1

SEQUENCE LISTING

```
<160> NUMBER OF SEQ ID NOS: 42

<210> SEQ ID NO 1
<211> LENGTH: 3033
<212> TYPE: DNA
<213> ORGANISM: Nicotiana tabacum
<220> FEATURE:
<221> NAME/KEY: CDS
```

-continued

<222> LOCATION: (22)..(2838)

<400> SEQUENCE: 1

```
ataaaggtta aagaaaaaaa a atg aat gaa aat ttg gag gaa cag agc aag          51
                         Met Asn Glu Asn Leu Glu Glu Gln Ser Lys
                         1               5                   10 ctt ccc gag ctt aaa ctg gat gct aag caa gct caa gga ttt ctc tca          99
Leu Pro Glu Leu Lys Leu Asp Ala Lys Gln Ala Gln Gly Phe Leu Ser
                15                  20                  25 ttc ttc aaa acc ctg ccc aag gac cct agg gca gtt cgc ctc ttt gat         147
Phe Phe Lys Thr Leu Pro Lys Asp Pro Arg Ala Val Arg Leu Phe Asp
        30                  35                  40 cgt cgg gac tat tat aca tct cat gga gat gat gca act ttc att gca         195
Arg Arg Asp Tyr Tyr Thr Ser His Gly Asp Asp Ala Thr Phe Ile Ala
    45                  50                  55 gag aca tat tac cac aca aca act gcg tta cga cag ttg ggt aat aga         243
Glu Thr Tyr Tyr His Thr Thr Thr Ala Leu Arg Gln Leu Gly Asn Arg
60                  65                  70 gct gat gcc ctt tcc agt gtt agt gtg agt aga aac atg ttt gaa aca         291
Ala Asp Ala Leu Ser Ser Val Ser Val Ser Arg Asn Met Phe Glu Thr
75                  80                  85                  90 ata gct cgt gac att ctc ttg gag aga atg gac cgt act ctt gaa cta         339
Ile Ala Arg Asp Ile Leu Leu Glu Arg Met Asp Arg Thr Leu Glu Leu
                95                  100                 105 tat gag ggc agt ggt tca aac tgg aga ctg gta aaa agt gga acc cca         387
Tyr Glu Gly Ser Gly Ser Asn Trp Arg Leu Val Lys Ser Gly Thr Pro
            110                 115                 120 ggg aat ctt gga agt ttt gag gat att ctg ttt gct aat aat gaa atg         435
Gly Asn Leu Gly Ser Phe Glu Asp Ile Leu Phe Ala Asn Asn Glu Met
        125                 130                 135 caa aat tct ccg gtg att gct gct ctt gct cca aac ttc ggt cag aat         483
Gln Asn Ser Pro Val Ile Ala Ala Leu Ala Pro Asn Phe Gly Gln Asn
    140                 145                 150 gga tgt gaa gtt ggc tta ggc tat gtt gat att act aag aga gtc ctt         531
Gly Cys Glu Val Gly Leu Gly Tyr Val Asp Ile Thr Lys Arg Val Leu
155                 160                 165                 170 ggt tta aca gaa ttt cta gat gat agc cac ttc aca aat ttg gag tct         579
Gly Leu Thr Glu Phe Leu Asp Asp Ser His Phe Thr Asn Leu Glu Ser
                175                 180                 185 gct ttg gtt gct ctt ggt tgc aga gaa tgt ctt gta cca gcg gag act         627
Ala Leu Val Ala Leu Gly Cys Arg Glu Cys Leu Val Pro Ala Glu Thr
            190                 195                 200 ggc aaa tcc agt gaa tac agg cct atg ttt gat gca ata tct aga tgc         675
Gly Lys Ser Ser Glu Tyr Arg Pro Met Phe Asp Ala Ile Ser Arg Cys
        205                 210                 215 ggc gtg atg gta act gaa aga aag aaa act gaa ttt aaa ggg aga gat         723
Gly Val Met Val Thr Glu Arg Lys Lys Thr Glu Phe Lys Gly Arg Asp
    220                 225                 230 ttg gta cag gat ctt ggt agg ctc gtc aag ggt tca gta gaa cct gtt         771
Leu Val Gln Asp Leu Gly Arg Leu Val Lys Gly Ser Val Glu Pro Val
235                 240                 245                 250 cga gat ttg gtc tct ggg ttc gaa tgt gca tca ggc gct ttg ggg tgc         819
Arg Asp Leu Val Ser Gly Phe Glu Cys Ala Ser Gly Ala Leu Gly Cys
                255                 260                 265 ata ctt tct tat gca gaa cta ctt gcg gat gag agc aac tat gga aac         867
Ile Leu Ser Tyr Ala Glu Leu Leu Ala Asp Glu Ser Asn Tyr Gly Asn
            270                 275                 280 tat aca gtc aaa caa tac aac ctc aat agt tac atg aga tta gat tct         915
Tyr Thr Val Lys Gln Tyr Asn Leu Asn Ser Tyr Met Arg Leu Asp Ser
        285                 290                 295
```

```
gct gct atg aga gca ctg aat gtt atg gag agc aaa tca gat gct aat    963
Ala Ala Met Arg Ala Leu Asn Val Met Glu Ser Lys Ser Asp Ala Asn
300             305                 310 aaa aat ttt agc ttg ttc ggt ctg atg aat aga acg tgt act gct gga   1011
Lys Asn Phe Ser Leu Phe Gly Leu Met Asn Arg Thr Cys Thr Ala Gly
315             320                 325                 330 atg ggt aaa agg tta ttg cac atg tgg ctg aag caa cct tta cta gat   1059
Met Gly Lys Arg Leu Leu His Met Trp Leu Lys Gln Pro Leu Leu Asp
            335                 340                 345 gta gaa gag att aac tgt agg ctg gat tta gtt caa tca ttc gtg gag   1107
Val Glu Glu Ile Asn Cys Arg Leu Asp Leu Val Gln Ser Phe Val Glu
        350                 355                 360 gat gct gcg ctt cgc caa gat ttg agg cag cat ctg aaa aga att tca   1155
Asp Ala Ala Leu Arg Gln Asp Leu Arg Gln His Leu Lys Arg Ile Ser
    365                 370                 375 gat att gag cgg ctg aca cac aat ctt gag agg aaa aga gcc agt tta   1203
Asp Ile Glu Arg Leu Thr His Asn Leu Glu Arg Lys Arg Ala Ser Leu
380                 385                 390 gtg cac gtt gta aaa ctc tat cag tca agt acc aga gta cca tat atc   1251
Val His Val Val Lys Leu Tyr Gln Ser Ser Thr Arg Val Pro Tyr Ile
395             400                 405                 410 aaa agt gtt ttg gaa cgt cat gat ggg caa ttt gca aca ctc atc agg   1299
Lys Ser Val Leu Glu Arg His Asp Gly Gln Phe Ala Thr Leu Ile Arg
            415                 420                 425 gaa agg tat att gat tct cta gag aaa tgg agt gat gat aat cac ctg   1347
Glu Arg Tyr Ile Asp Ser Leu Glu Lys Trp Ser Asp Asp Asn His Leu
        430                 435                 440 aat aag ttc ata ggt ctt gtg gaa act tct gtt gac ctt gat caa ctt   1395
Asn Lys Phe Ile Gly Leu Val Glu Thr Ser Val Asp Leu Asp Gln Leu
    445                 450                 455 gag aat gga gaa tac atg att tct tct gca tat gac cca aat tta tct   1443
Glu Asn Gly Glu Tyr Met Ile Ser Ser Ala Tyr Asp Pro Asn Leu Ser
460                 465                 470 gct ctg aag gat gag caa gag aca ttg gag cga caa att cat aat ttg   1491
Ala Leu Lys Asp Glu Gln Glu Thr Leu Glu Arg Gln Ile His Asn Leu
475             480                 485                 490 cac aaa caa act gcc aat gat ctt gat cta cct att gat aag tca ctt   1539
His Lys Gln Thr Ala Asn Asp Leu Asp Leu Pro Ile Asp Lys Ser Leu
            495                 500                 505 aaa cta gat aaa gaa aca caa ttt gga cac gtc ttc aga att acc aag   1587
Lys Leu Asp Lys Glu Thr Gln Phe Gly His Val Phe Arg Ile Thr Lys
        510                 515                 520 aaa gaa gaa cca aaa gtc agg aag cag cta aat tct cac tac att gtt   1635
Lys Glu Glu Pro Lys Val Arg Lys Gln Leu Asn Ser His Tyr Ile Val
    525                 530                 535 ctc gaa aca cgt aag gat ggg gta aag ttc acc tat aca aaa ctc aaa   1683
Leu Glu Thr Arg Lys Asp Gly Val Lys Phe Thr Tyr Thr Lys Leu Lys
540                 545                 550 aaa cta gga gat cag ttc cag aag att gta gag gag tac aaa agc tgt   1731
Lys Leu Gly Asp Gln Phe Gln Lys Ile Val Glu Glu Tyr Lys Ser Cys
555             560                 565                 570 cag aaa gaa ttg gta gct cgt gta gtt caa aca gct gcg agt ttc tcc   1779
Gln Lys Glu Leu Val Ala Arg Val Val Gln Thr Ala Ala Ser Phe Ser
            575                 580                 585 gag gtg ttt gca ggt ata gct ggt gta ctt gct gag ttg gat gtg tta   1827
Glu Val Phe Ala Gly Ile Ala Gly Val Leu Ala Glu Leu Asp Val Leu
        590                 595                 600 ctg agt ttt gcg gat ttg gct gcc agt tgc cca act ccc tac aca aga   1875
Leu Ser Phe Ala Asp Leu Ala Ala Ser Cys Pro Thr Pro Tyr Thr Arg
```

-continued

```
               605                 610                 615
cca aat atc agt cca cca gat aca gga gat att ata ctt gaa ggg tgt    1923
Pro Asn Ile Ser Pro Pro Asp Thr Gly Asp Ile Ile Leu Glu Gly Cys
        620                 625                 630 agg cat cct tgt gtg gaa gct caa gat tgg gtt aac tcc att cct aat    1971
Arg His Pro Cys Val Glu Ala Gln Asp Trp Val Asn Ser Ile Pro Asn
635                 640                 645                 650 gac tgt aga cta gtt agg gga gag agt tgg ttt cag att atc aca ggc    2019
Asp Cys Arg Leu Val Arg Gly Glu Ser Trp Phe Gln Ile Ile Thr Gly
                655                 660                 665 cct aac atg ggt gga aag tcg acc tac att cgg cag gtt ggt gtg aat    2067
Pro Asn Met Gly Gly Lys Ser Thr Tyr Ile Arg Gln Val Gly Val Asn
        670                 675                 680 gtc ctg atg gcc caa gtt ggc tcg ttt gtt cca tgt gac aat gct acc    2115
Val Leu Met Ala Gln Val Gly Ser Phe Val Pro Cys Asp Asn Ala Thr
685                 690                 695 att tct att cgt gat tgt att ttt gct cgt gtt ggc gct gga gat tgc    2163
Ile Ser Ile Arg Asp Cys Ile Phe Ala Arg Val Gly Ala Gly Asp Cys
                700                 705                 710 cag ctg aga gga gtt tct act ttt atg caa gag atg ctt gag act gca    2211
Gln Leu Arg Gly Val Ser Thr Phe Met Gln Glu Met Leu Glu Thr Ala
715                 720                 725                 730 tcg atc ttg aaa gga gct act gat aga tca ttg att ata att gat gag    2259
Ser Ile Leu Lys Gly Ala Thr Asp Arg Ser Leu Ile Ile Ile Asp Glu
                735                 740                 745 ttg ggc cgt ggg aca tca acc tac gat ggc ttt ggt tta gct tgg gct    2307
Leu Gly Arg Gly Thr Ser Thr Tyr Asp Gly Phe Gly Leu Ala Trp Ala
        750                 755                 760 att tgt gag cac att gtt gaa gaa att aaa gca cca aca ttg ttt gcc    2355
Ile Cys Glu His Ile Val Glu Glu Ile Lys Ala Pro Thr Leu Phe Ala
765                 770                 775 act cac ttt cat gag ctg act gca tta gcc aac aag aat gga gac aat    2403
Thr His Phe His Glu Leu Thr Ala Leu Ala Asn Lys Asn Gly Asp Asn
                780                 785                 790 gga cat aag aaa aat gct ggg ata gca aat ttt cat gtt ttt gca cac    2451
Gly His Lys Lys Asn Ala Gly Ile Ala Asn Phe His Val Phe Ala His
795                 800                 805                 810 att gac cct tct aat cgc aag cta act atg ctt tac aag gtt cac cca    2499
Ile Asp Pro Ser Asn Arg Lys Leu Thr Met Leu Tyr Lys Val His Pro
                815                 820                 825 ggt gct tgt gat cag agt ttt ggt att cat gtt gct gaa ttt gca aat    2547
Gly Ala Cys Asp Gln Ser Phe Gly Ile His Val Ala Glu Phe Ala Asn
        830                 835                 840 ttt cca ccg agt gtt gtg gct ctg gct aga gaa aag gca tct gag ttg    2595
Phe Pro Pro Ser Val Val Ala Leu Ala Arg Glu Lys Ala Ser Glu Leu
845                 850                 855 gag gat ttc tct cct att gcc ata att cca aat gac att aaa gag gca    2643
Glu Asp Phe Ser Pro Ile Ala Ile Ile Pro Asn Asp Ile Lys Glu Ala
                860                 865                 870 gct tca aaa cgg aag aga gaa ttt gac cgc cat gac gtg tct aga ggt    2691
Ala Ser Lys Arg Lys Arg Glu Phe Asp Arg His Asp Val Ser Arg Gly
875                 880                 885                 890 act gcc aga gct cgg caa ttc tta cag gat ttc gct cag ttg cca ctg    2739
Thr Ala Arg Ala Arg Gln Phe Leu Gln Asp Phe Ala Gln Leu Pro Leu
                895                 900                 905 gat aag atg gat cca aac gtg gtc agg caa aag ttg agc aaa atg aaa    2787
Asp Lys Met Asp Pro Asn Val Val Arg Gln Lys Leu Ser Lys Met Lys
        910                 915                 920 acc gac ctg gag agg gat gca gtt gac tct cac tgg ctt cag caa ttc    2835
```

-continued

```
Thr Asp Leu Glu Arg Asp Ala Val Asp Ser His Trp Leu Gln Gln Phe
        925                 930                 935
ttt taattcttca gattagaact atcttctatt ctgtgaagct tggggggggaa       2888
Phe
tgatacttat gggttttgtg gatataactt agcctatctg taaactttca tttaaatcct 2948 taccccaaac atgattctct gtaatcaggg gactttgta tgcattctgt gttaatagta  3008
agcgttatct tatatggtca aaaaa                                       3033

<210> SEQ ID NO 2
<211> LENGTH: 939
<212> TYPE: PRT
<213> ORGANISM: Nicotiana tabacum

<400> SEQUENCE: 2

Met Asn Glu Asn Leu Glu Glu Gln Ser Lys Leu Pro Glu Leu Lys Leu
1               5                   10                  15

Asp Ala Lys Gln Ala Gln Gly Phe Leu Ser Phe Phe Lys Thr Leu Pro
                20                  25                  30

Lys Asp Pro Arg Ala Val Arg Leu Phe Asp Arg Arg Asp Tyr Tyr Thr
            35                  40                  45

Ser His Gly Asp Asp Ala Thr Phe Ile Ala Glu Thr Tyr His Thr
        50                  55                  60

Thr Thr Ala Leu Arg Gln Leu Gly Asn Arg Ala Asp Ala Leu Ser Ser
65                  70                  75                  80

Val Ser Val Ser Arg Asn Met Phe Glu Thr Ile Ala Arg Asp Ile Leu
                85                  90                  95

Leu Glu Arg Met Asp Arg Thr Leu Glu Leu Tyr Glu Gly Ser Gly Ser
            100                 105                 110

Asn Trp Arg Leu Val Lys Ser Gly Thr Pro Gly Asn Leu Gly Ser Phe
        115                 120                 125

Glu Asp Ile Leu Phe Ala Asn Asn Glu Met Gln Asn Ser Pro Val Ile
    130                 135                 140

Ala Ala Leu Ala Pro Asn Phe Gly Gln Asn Gly Cys Glu Val Gly Leu
145                 150                 155                 160

Gly Tyr Val Asp Ile Thr Lys Arg Val Leu Gly Leu Thr Glu Phe Leu
                165                 170                 175

Asp Asp Ser His Phe Thr Asn Leu Glu Ser Ala Leu Val Ala Leu Gly
            180                 185                 190

Cys Arg Glu Cys Leu Val Pro Ala Glu Thr Gly Lys Ser Ser Glu Tyr
        195                 200                 205

Arg Pro Met Phe Asp Ala Ile Ser Arg Cys Gly Val Met Val Thr Glu
    210                 215                 220

Arg Lys Lys Thr Glu Phe Lys Gly Arg Asp Leu Val Gln Asp Leu Gly
225                 230                 235                 240

Arg Leu Val Lys Gly Ser Val Glu Pro Val Arg Asp Leu Val Ser Gly
                245                 250                 255

Phe Glu Cys Ala Ser Gly Ala Leu Gly Cys Ile Leu Ser Tyr Ala Glu
            260                 265                 270

Leu Leu Ala Asp Glu Ser Asn Tyr Gly Asn Tyr Thr Val Lys Gln Tyr
        275                 280                 285

Asn Leu Asn Ser Tyr Met Arg Leu Asp Ser Ala Ala Met Arg Ala Leu
    290                 295                 300

Asn Val Met Glu Ser Lys Ser Asp Ala Asn Lys Asn Phe Ser Leu Phe
```

-continued

```
                305                 310                 315                 320
Gly Leu Met Asn Arg Thr Cys Thr Ala Gly Met Gly Lys Arg Leu Leu
                    325                 330                 335

His Met Trp Leu Lys Gln Pro Leu Leu Asp Val Glu Glu Ile Asn Cys
                340                 345                 350

Arg Leu Asp Leu Val Gln Ser Phe Val Glu Asp Ala Ala Leu Arg Gln
                355                 360                 365

Asp Leu Arg Gln His Leu Lys Arg Ile Ser Asp Ile Glu Arg Leu Thr
                370                 375                 380

His Asn Leu Glu Arg Lys Arg Ala Ser Leu Val His Val Val Lys Leu
385                 390                 395                 400

Tyr Gln Ser Ser Thr Arg Val Pro Tyr Ile Lys Ser Val Leu Glu Arg
                    405                 410                 415

His Asp Gly Gln Phe Ala Thr Leu Ile Arg Glu Arg Tyr Ile Asp Ser
                    420                 425                 430

Leu Glu Lys Trp Ser Asp Asp Asn His Leu Asn Lys Phe Ile Gly Leu
                435                 440                 445

Val Glu Thr Ser Val Asp Leu Asp Gln Leu Glu Asn Gly Glu Tyr Met
            450                 455                 460

Ile Ser Ser Ala Tyr Asp Pro Asn Leu Ser Ala Leu Lys Asp Glu Gln
465                 470                 475                 480

Glu Thr Leu Glu Arg Gln Ile His Asn Leu His Lys Gln Thr Ala Asn
                        485                 490                 495

Asp Leu Asp Leu Pro Ile Asp Lys Ser Leu Lys Leu Asp Lys Glu Thr
                500                 505                 510

Gln Phe Gly His Val Phe Arg Ile Thr Lys Lys Glu Glu Pro Lys Val
                515                 520                 525

Arg Lys Gln Leu Asn Ser His Tyr Ile Val Leu Glu Thr Arg Lys Asp
                530                 535                 540

Gly Val Lys Phe Thr Tyr Thr Lys Leu Lys Lys Leu Gly Asp Gln Phe
545                 550                 555                 560

Gln Lys Ile Val Glu Glu Tyr Lys Ser Cys Gln Lys Glu Leu Val Ala
                    565                 570                 575

Arg Val Val Gln Thr Ala Ala Ser Phe Ser Glu Val Phe Ala Gly Ile
                    580                 585                 590

Ala Gly Val Leu Ala Glu Leu Asp Val Leu Leu Ser Phe Ala Asp Leu
                595                 600                 605

Ala Ala Ser Cys Pro Thr Pro Tyr Thr Arg Pro Asn Ile Ser Pro Pro
            610                 615                 620

Asp Thr Gly Asp Ile Ile Leu Glu Gly Cys Arg His Pro Cys Val Glu
625                 630                 635                 640

Ala Gln Asp Trp Val Asn Ser Ile Pro Asn Asp Cys Arg Leu Val Arg
                    645                 650                 655

Gly Glu Ser Trp Phe Gln Ile Ile Thr Gly Pro Asn Met Gly Gly Lys
                    660                 665                 670

Ser Thr Tyr Ile Arg Gln Val Gly Val Asn Val Leu Met Ala Gln Val
                675                 680                 685

Gly Ser Phe Val Pro Cys Asp Asn Ala Thr Ile Ser Ile Arg Asp Cys
            690                 695                 700

Ile Phe Ala Arg Val Gly Ala Gly Asp Cys Gln Leu Arg Gly Val Ser
705                 710                 715                 720

Thr Phe Met Gln Glu Met Leu Glu Thr Ala Ser Ile Leu Lys Gly Ala
                    725                 730                 735
```

-continued

```
Thr Asp Arg Ser Leu Ile Ile Ile Asp Glu Leu Gly Arg Gly Thr Ser
        740                 745                 750
Thr Tyr Asp Gly Phe Gly Leu Ala Trp Ala Ile Cys Glu His Ile Val
            755                 760                 765
Glu Glu Ile Lys Ala Pro Thr Leu Phe Ala Thr His Phe His Glu Leu
        770                 775                 780
Thr Ala Leu Ala Asn Lys Asn Gly Asp Asn Gly His Lys Lys Asn Ala
785                 790                 795                 800
Gly Ile Ala Asn Phe His Val Phe Ala His Ile Asp Pro Ser Asn Arg
                805                 810                 815
Lys Leu Thr Met Leu Tyr Lys Val His Pro Gly Ala Cys Asp Gln Ser
            820                 825                 830
Phe Gly Ile His Val Ala Glu Phe Ala Asn Phe Pro Pro Ser Val Val
        835                 840                 845
Ala Leu Ala Arg Glu Lys Ala Ser Glu Leu Glu Asp Phe Ser Pro Ile
    850                 855                 860
Ala Ile Ile Pro Asn Asp Ile Lys Glu Ala Ala Ser Lys Arg Lys Arg
865                 870                 875                 880
Glu Phe Asp Arg His Asp Val Ser Arg Gly Thr Ala Arg Ala Arg Gln
                885                 890                 895
Phe Leu Gln Asp Phe Ala Gln Leu Pro Leu Asp Lys Met Asp Pro Asn
            900                 905                 910
Val Val Arg Gln Lys Leu Ser Lys Met Lys Thr Asp Leu Glu Arg Asp
        915                 920                 925
Ala Val Asp Ser His Trp Leu Gln Gln Phe Phe
    930                 935
```

<210> SEQ ID NO 3
<211> LENGTH: 3033
<212> TYPE: DNA
<213> ORGANISM: Nicotiana tabacum
<220> FEATURE:
<221> NAME/KEY: CDS
<222> LOCATION: (22)..(2838)

<400> SEQUENCE: 3

```
aaagttaaaa gaaaaaaaaa a atg aat gaa aat ttg gag gaa cag agc aag        51
                        Met Asn Glu Asn Leu Glu Glu Gln Ser Lys
                          1               5                  10 ctt cct gag ctt aaa ctt gat gct aag caa gct caa gga ttt ctc tca        99
Leu Pro Glu Leu Lys Leu Asp Ala Lys Gln Ala Gln Gly Phe Leu Ser
             15                  20                  25 ttt ttc aaa acc cta ccc aag gac cct agg gca gtt cgc ctc ttt gat      147
Phe Phe Lys Thr Leu Pro Lys Asp Pro Arg Ala Val Arg Leu Phe Asp
         30                  35                  40 cgt cgg gac tat tat act gct cat gga gat gat gca act ttc att gca      195
Arg Arg Asp Tyr Tyr Thr Ala His Gly Asp Asp Ala Thr Phe Ile Ala
     45                  50                  55 gag aca tat tac cac aca aca act gcg tta cga cag ttg ggt aat aga      243
Glu Thr Tyr Tyr His Thr Thr Thr Ala Leu Arg Gln Leu Gly Asn Arg
 60                  65                  70 gct gat gcc ctt tcc agt gtt agt gtg agt aga aac atg ttt gaa aca      291
Ala Asp Ala Leu Ser Ser Val Ser Val Ser Arg Asn Met Phe Glu Thr
 75                  80                  85                  90 ata gct cgt gac att ctc ttg gag aga atg gac cgt act ctt gaa cta      339
Ile Ala Arg Asp Ile Leu Leu Glu Arg Met Asp Arg Thr Leu Glu Leu
                 95                 100                 105
```

```
tat gag ggc agt ggt tca aac tgg aga ctg gta aaa agt gga acc cca        387
Tyr Glu Gly Ser Gly Ser Asn Trp Arg Leu Val Lys Ser Gly Thr Pro
            110                 115                 120 ggg aat ctt gga agt ttt gag gat att ctg ttt gct aat aat gaa atg        435
Gly Asn Leu Gly Ser Phe Glu Asp Ile Leu Phe Ala Asn Asn Glu Met
            125                 130                 135 caa aat tct ccg gtg att gct gct ctt gct cca aac ttc ggt cag aat        483
Gln Asn Ser Pro Val Ile Ala Ala Leu Ala Pro Asn Phe Gly Gln Asn
        140                 145                 150 gga tgt gaa gtt ggc tta ggc tat gtt gat att act aag aga gtc ctt        531
Gly Cys Glu Val Gly Leu Gly Tyr Val Asp Ile Thr Lys Arg Val Leu
155                 160                 165                 170 ggt tta aca gaa ttt cta gat gat agc cac ttc aca aat ttg gag tct        579
Gly Leu Thr Glu Phe Leu Asp Asp Ser His Phe Thr Asn Leu Glu Ser
                175                 180                 185 gct ttg gtt gct ctt ggt tgc aga gaa tgt ctt gta cca gcg gag act        627
Ala Leu Val Ala Leu Gly Cys Arg Glu Cys Leu Val Pro Ala Glu Thr
                190                 195                 200 ggc aaa tcc agt gaa tac agg cct atg ttt gat gca ata tct aga tgc        675
Gly Lys Ser Ser Glu Tyr Arg Pro Met Phe Asp Ala Ile Ser Arg Cys
            205                 210                 215 ggc gtg atg gta act gaa aga aag aaa act gaa ttt aaa ggg aga gat        723
Gly Val Met Val Thr Glu Arg Lys Lys Thr Glu Phe Lys Gly Arg Asp
        220                 225                 230 ttg gta cag gat ctt ggt agg ctc gtc aag ggt tca gta gaa cct gtt        771
Leu Val Gln Asp Leu Gly Arg Leu Val Lys Gly Ser Val Glu Pro Val
235                 240                 245                 250 cga gat ttg gtc tct ggg ttc gaa tgt gca tca ggc gct ttg ggg tgc        819
Arg Asp Leu Val Ser Gly Phe Glu Cys Ala Ser Gly Ala Leu Gly Cys
                255                 260                 265 ata ctt tct tat gca gaa cta ctt gcg gat gag agc aac tat gga aac        867
Ile Leu Ser Tyr Ala Glu Leu Leu Ala Asp Glu Ser Asn Tyr Gly Asn
                270                 275                 280 tat aca gtc aaa caa tac aac ctc aat agt tac atg aga tta gat tct        915
Tyr Thr Val Lys Gln Tyr Asn Leu Asn Ser Tyr Met Arg Leu Asp Ser
            285                 290                 295 gct gct atg aga gca ctg aat gtt atg gag agc aaa tca gat gct aat        963
Ala Ala Met Arg Ala Leu Asn Val Met Glu Ser Lys Ser Asp Ala Asn
        300                 305                 310 aaa aat ttt agc ttg ttc ggt ctg atg aat aga acg tgt act gct gga       1011
Lys Asn Phe Ser Leu Phe Gly Leu Met Asn Arg Thr Cys Thr Ala Gly
315                 320                 325                 330 atg ggt aaa agg tta ttg cac atg tgg ctg aag caa cct tta cta gat       1059
Met Gly Lys Arg Leu Leu His Met Trp Leu Lys Gln Pro Leu Leu Asp
                335                 340                 345 gta gaa gag att aac tgt agg ctg gat tta gtt caa tca ttc gtg gag       1107
Val Glu Glu Ile Asn Cys Arg Leu Asp Leu Val Gln Ser Phe Val Glu
                350                 355                 360 gat gct gcg ctt cgc caa gat ttg agg cag cat ctg aaa aga att tca       1155
Asp Ala Ala Leu Arg Gln Asp Leu Arg Gln His Leu Lys Arg Ile Ser
            365                 370                 375 gat att gag cgg ctg aca cac aat ctt gag agg aaa aga gcc agt tta       1203
Asp Ile Glu Arg Leu Thr His Asn Leu Glu Arg Lys Arg Ala Ser Leu
        380                 385                 390 gtg cac gtt gta aaa ctc tat cag tca agt acc aga gta cca tat atc       1251
Val His Val Val Lys Leu Tyr Gln Ser Ser Thr Arg Val Pro Tyr Ile
395                 400                 405                 410 aaa agt gtt ttg gaa cgt cat gat ggg caa ttt gca aca ctc atc agg       1299
Lys Ser Val Leu Glu Arg His Asp Gly Gln Phe Ala Thr Leu Ile Arg
                415                 420                 425
```

-continued

| | |
|---|---|
| gaa agg tat att gat tct cta gag aaa tgg agt gat gat aat cac ctg<br>Glu Arg Tyr Ile Asp Ser Leu Glu Lys Trp Ser Asp Asp Asn His Leu<br>430                             435                        440 | 1347 |
| aat aag ttc ata ggt ctt gtg gaa act tct gtt gac ctt gat caa ctt<br>Asn Lys Phe Ile Gly Leu Val Glu Thr Ser Val Asp Leu Asp Gln Leu<br>445                           450                        455 | 1395 |
| gag aat gga gaa tac atg att tct tct gca tat gac cca aat tta tct<br>Glu Asn Gly Glu Tyr Met Ile Ser Ser Ala Tyr Asp Pro Asn Leu Ser<br>460                           465                        470 | 1443 |
| gct ctg aag gat gag caa gag aca ttg gag cga caa att cat aat ttg<br>Ala Leu Lys Asp Glu Gln Glu Thr Leu Glu Arg Gln Ile His Asn Leu<br>475                         480                        485                        490 | 1491 |
| cac aaa caa act gcc aat gat ctt gat cta cct att gat aag tca ctt<br>His Lys Gln Thr Ala Asn Asp Leu Asp Leu Pro Ile Asp Lys Ser Leu<br>                         495                        500                        505 | 1539 |
| aaa cta gat aaa gaa aca caa ttt gga cac gtc ttc aga att acc aag<br>Lys Leu Asp Lys Glu Thr Gln Phe Gly His Val Phe Arg Ile Thr Lys<br>510                           515                        520 | 1587 |
| aaa gaa gaa cca aaa gtc agg aag cag cta aat tct cac tac att gtt<br>Lys Glu Glu Pro Lys Val Arg Lys Gln Leu Asn Ser His Tyr Ile Val<br>525                         530                        535 | 1635 |
| ctc gaa aca cgt aag gat ggg gta aag ttc acc tat aca aaa ctc aaa<br>Leu Glu Thr Arg Lys Asp Gly Val Lys Phe Thr Tyr Thr Lys Leu Lys<br>540                         545                        550 | 1683 |
| aaa cta gga gat cag ttc cag aag att gta gag gag tac aaa agc tgt<br>Lys Leu Gly Asp Gln Phe Gln Lys Ile Val Glu Glu Tyr Lys Ser Cys<br>555                         560                        565                        570 | 1731 |
| cag aaa gaa ttg gta gct cgt gta gtt caa aca gct gcg agt ttc tcc<br>Gln Lys Glu Leu Val Ala Arg Val Val Gln Thr Ala Ala Ser Phe Ser<br>                         575                        580                        585 | 1779 |
| gag gtg ttt gca ggt ata gct ggt gta ctt gct gag ttg gat gtg tta<br>Glu Val Phe Ala Gly Ile Ala Gly Val Leu Ala Glu Leu Asp Val Leu<br>590                           595                        600 | 1827 |
| ctg agt ttt gcg gat ttg gct gcc agt tgc cca act ccc tac aca aga<br>Leu Ser Phe Ala Asp Leu Ala Ala Ser Cys Pro Thr Pro Tyr Thr Arg<br>605                         610                        615 | 1875 |
| cca aat atc agt cca cca gat aca gga gat att ata ctt gaa ggg tgt<br>Pro Asn Ile Ser Pro Pro Asp Thr Gly Asp Ile Ile Leu Glu Gly Cys<br>620                           625                        630 | 1923 |
| agg cat cct tgt gtg gaa gct caa gat tgg gtt aac tcc att cct aat<br>Arg His Pro Cys Val Glu Ala Gln Asp Trp Val Asn Ser Ile Pro Asn<br>635                         640                        645                        650 | 1971 |
| gac tgt aga cta gtt agg gga gag agt tgg ttt cag att atc aca ggc<br>Asp Cys Arg Leu Val Arg Gly Glu Ser Trp Phe Gln Ile Ile Thr Gly<br>                         655                        660                        665 | 2019 |
| cct aac atg ggt gga aag tcg acc tac att cgg cag gtt ggt gtg aat<br>Pro Asn Met Gly Gly Lys Ser Thr Tyr Ile Arg Gln Val Gly Val Asn<br>670                           675                        680 | 2067 |
| gtc ctg atg gcc caa gtt ggc tcg ttt gtt cca tgt gac aat gct acc<br>Val Leu Met Ala Gln Val Gly Ser Phe Val Pro Cys Asp Asn Ala Thr<br>685                         690                        695 | 2115 |
| att tct att cgt gat tgt att ttt gct cgt gtt ggc gct gga gat tgc<br>Ile Ser Ile Arg Asp Cys Ile Phe Ala Arg Val Gly Ala Gly Asp Cys<br>700                         705                        710 | 2163 |
| cag ctg aga gga gtt tct act ttt atg caa gag atg ctt gag act gca<br>Gln Leu Arg Gly Val Ser Thr Phe Met Gln Glu Met Leu Glu Thr Ala<br>715                         720                        725                        730 | 2211 |
| tcg atc ttg aaa gga gct act gat aga tca ttg att ata att gat gag<br>Ser Ile Leu Lys Gly Ala Thr Asp Arg Ser Leu Ile Ile Ile Asp Glu | 2259 |

-continued

```
                735                 740                 745
ttg ggc cgt ggg aca tca acc tac gat ggc ttt ggt tta gct tgg gct    2307
Leu Gly Arg Gly Thr Ser Thr Tyr Asp Gly Phe Gly Leu Ala Trp Ala
            750                 755                 760 att tgt gag cac att gtt gaa gaa att aaa gca cca aca ttg ttt gcc    2355
Ile Cys Glu His Ile Val Glu Glu Ile Lys Ala Pro Thr Leu Phe Ala
        765                 770                 775 act cac ttt cat gag ctg act gca tta gcc aac aag aat gga gac aat    2403
Thr His Phe His Glu Leu Thr Ala Leu Ala Asn Lys Asn Gly Asp Asn
    780                 785                 790 gga cat aag aaa aat gct ggg ata gca aat ttt cat gtt ttt gca cac    2451
Gly His Lys Lys Asn Ala Gly Ile Ala Asn Phe His Val Phe Ala His
795                 800                 805                 810 att gac cct tct aat cgc aag cta act atg ctt tac aag gtt cac cca    2499
Ile Asp Pro Ser Asn Arg Lys Leu Thr Met Leu Tyr Lys Val His Pro
                815                 820                 825 ggt gct tgt gat cag agt ttt ggt att cat gtt gct gaa ttt gca aat    2547
Gly Ala Cys Asp Gln Ser Phe Gly Ile His Val Ala Glu Phe Ala Asn
            830                 835                 840 ttt cca ccg agt gtt gtg gct ctg gct aga gaa aag gca tct gag ttg    2595
Phe Pro Pro Ser Val Val Ala Leu Ala Arg Glu Lys Ala Ser Glu Leu
        845                 850                 855 gag gat ttc tct cct att gcc ata att cca aat gac att aaa gag gca    2643
Glu Asp Phe Ser Pro Ile Ala Ile Ile Pro Asn Asp Ile Lys Glu Ala
    860                 865                 870 gct tca aaa cgg aag aga gaa ttt gac cgc cat gac gtg tct aga ggt    2691
Ala Ser Lys Arg Lys Arg Glu Phe Asp Arg His Asp Val Ser Arg Gly
875                 880                 885                 890 act gcc aga gct cgg caa ttc tta cag gat ttc gct cag ttg cca ctg    2739
Thr Ala Arg Ala Arg Gln Phe Leu Gln Asp Phe Ala Gln Leu Pro Leu
                895                 900                 905 gat aag atg gat cca aac gtg gtc agg caa aag ttg agc aaa atg aaa    2787
Asp Lys Met Asp Pro Asn Val Val Arg Gln Lys Leu Ser Lys Met Lys
            910                 915                 920 acc gac ctg gag agg gat gca gtt gac tct cac tgg ctt cag caa ttc    2835
Thr Asp Leu Glu Arg Asp Ala Val Asp Ser His Trp Leu Gln Gln Phe
        925                 930                 935 ttt taattcttca gattagaact atcttctatt ctgtgaagct tggggggaa          2888
Phe tgatacttat gggttttgtg gatataactt agcctatctg taaactttca tttaaatcct  2948 tacccccaaac atgattctct gtaatcaggg gacttttgta tgcattctgt gttaatagta 3008 agcgttatct tatatggtca aaaaa                                       3033

<210> SEQ ID NO 4
<211> LENGTH: 939
<212> TYPE: PRT
<213> ORGANISM: Nicotiana tabacum

<400> SEQUENCE: 4

Met Asn Glu Asn Leu Glu Glu Gln Ser Lys Leu Pro Glu Leu Lys Leu
1               5                   10                  15

Asp Ala Lys Gln Ala Gln Gly Phe Leu Ser Phe Phe Lys Thr Leu Pro
            20                  25                  30

Lys Asp Pro Arg Ala Val Arg Leu Phe Asp Arg Arg Tyr Tyr Thr
        35                  40                  45

Ala His Gly Asp Asp Ala Thr Phe Ile Ala Glu Thr Tyr Tyr His Thr
    50                  55                  60
```

-continued

Thr Thr Ala Leu Arg Gln Leu Gly Asn Arg Ala Asp Ala Leu Ser Ser
65                  70                  75                  80

Val Ser Val Ser Arg Asn Met Phe Glu Thr Ile Ala Arg Asp Ile Leu
                85                  90                  95

Leu Glu Arg Met Asp Arg Thr Leu Glu Leu Tyr Glu Gly Ser Gly Ser
            100                 105                 110

Asn Trp Arg Leu Val Lys Ser Gly Thr Pro Gly Asn Leu Gly Ser Phe
        115                 120                 125

Glu Asp Ile Leu Phe Ala Asn Asn Glu Met Gln Asn Ser Pro Val Ile
    130                 135                 140

Ala Ala Leu Ala Pro Asn Phe Gly Gln Asn Gly Cys Glu Val Gly Leu
145                 150                 155                 160

Gly Tyr Val Asp Ile Thr Lys Arg Val Leu Gly Leu Thr Glu Phe Leu
                165                 170                 175

Asp Asp Ser His Phe Thr Asn Leu Glu Ser Ala Leu Val Ala Leu Gly
            180                 185                 190

Cys Arg Glu Cys Leu Val Pro Ala Glu Thr Gly Lys Ser Ser Glu Tyr
        195                 200                 205

Arg Pro Met Phe Asp Ala Ile Ser Arg Cys Gly Val Met Val Thr Glu
    210                 215                 220

Arg Lys Lys Thr Glu Phe Lys Gly Arg Asp Leu Val Gln Asp Leu Gly
225                 230                 235                 240

Arg Leu Val Lys Gly Ser Val Glu Pro Val Arg Asp Leu Val Ser Gly
                245                 250                 255

Phe Glu Cys Ala Ser Gly Ala Leu Gly Cys Ile Leu Ser Tyr Ala Glu
            260                 265                 270

Leu Leu Ala Asp Glu Ser Asn Tyr Gly Asn Tyr Thr Val Lys Gln Tyr
        275                 280                 285

Asn Leu Asn Ser Tyr Met Arg Leu Asp Ser Ala Ala Met Arg Ala Leu
    290                 295                 300

Asn Val Met Glu Ser Lys Ser Asp Ala Asn Lys Asn Phe Ser Leu Phe
305                 310                 315                 320

Gly Leu Met Asn Arg Thr Cys Thr Ala Gly Met Gly Lys Arg Leu Leu
                325                 330                 335

His Met Trp Leu Lys Gln Pro Leu Leu Asp Val Glu Glu Ile Asn Cys
            340                 345                 350

Arg Leu Asp Leu Val Gln Ser Phe Val Glu Asp Ala Ala Leu Arg Gln
        355                 360                 365

Asp Leu Arg Gln His Leu Lys Arg Ile Ser Asp Ile Glu Arg Leu Thr
    370                 375                 380

His Asn Leu Glu Arg Lys Arg Ala Ser Leu Val His Val Val Lys Leu
385                 390                 395                 400

Tyr Gln Ser Ser Thr Arg Val Pro Tyr Ile Lys Ser Val Leu Glu Arg
                405                 410                 415

His Asp Gly Gln Phe Ala Thr Leu Ile Arg Glu Arg Tyr Ile Asp Ser
            420                 425                 430

Leu Glu Lys Trp Ser Asp Asp Asn His Leu Asn Lys Phe Ile Gly Leu
        435                 440                 445

Val Glu Thr Ser Val Asp Leu Asp Gln Leu Glu Asn Gly Glu Tyr Met
    450                 455                 460

Ile Ser Ser Ala Tyr Asp Pro Asn Leu Ser Ala Leu Lys Asp Glu Gln
465                 470                 475                 480

Glu Thr Leu Glu Arg Gln Ile His Asn Leu His Lys Gln Thr Ala Asn

-continued

```
                485                 490                 495
Asp Leu Asp Leu Pro Ile Asp Lys Ser Leu Lys Leu Asp Lys Glu Thr
                500                 505                 510

Gln Phe Gly His Val Phe Arg Ile Thr Lys Lys Glu Glu Pro Lys Val
            515                 520                 525

Arg Lys Gln Leu Asn Ser His Tyr Ile Val Leu Glu Thr Arg Lys Asp
        530                 535                 540

Gly Val Lys Phe Thr Tyr Thr Lys Leu Lys Lys Leu Gly Asp Gln Phe
545                 550                 555                 560

Gln Lys Ile Val Glu Glu Tyr Lys Ser Cys Gln Lys Glu Leu Val Ala
                565                 570                 575

Arg Val Val Gln Thr Ala Ala Ser Phe Ser Glu Val Phe Ala Gly Ile
            580                 585                 590

Ala Gly Val Leu Ala Glu Leu Asp Val Leu Leu Ser Phe Ala Asp Leu
        595                 600                 605

Ala Ala Ser Cys Pro Thr Pro Tyr Thr Arg Pro Asn Ile Ser Pro Pro
        610                 615                 620

Asp Thr Gly Asp Ile Ile Leu Glu Gly Cys Arg His Pro Cys Val Glu
625                 630                 635                 640

Ala Gln Asp Trp Val Asn Ser Ile Pro Asn Asp Cys Arg Leu Val Arg
                645                 650                 655

Gly Glu Ser Trp Phe Gln Ile Ile Thr Gly Pro Asn Met Gly Gly Lys
            660                 665                 670

Ser Thr Tyr Ile Arg Gln Val Gly Val Asn Val Leu Met Ala Gln Val
        675                 680                 685

Gly Ser Phe Val Pro Cys Asp Asn Ala Thr Ile Ser Ile Arg Asp Cys
        690                 695                 700

Ile Phe Ala Arg Val Gly Ala Gly Asp Cys Gln Leu Arg Gly Val Ser
705                 710                 715                 720

Thr Phe Met Gln Glu Met Leu Glu Thr Ala Ser Ile Leu Lys Gly Ala
                725                 730                 735

Thr Asp Arg Ser Leu Ile Ile Ile Asp Glu Leu Gly Arg Gly Thr Ser
            740                 745                 750

Thr Tyr Asp Gly Phe Gly Leu Ala Trp Ala Ile Cys Glu His Ile Val
        755                 760                 765

Glu Glu Ile Lys Ala Pro Thr Leu Phe Ala Thr His Phe His Glu Leu
770                 775                 780

Thr Ala Leu Ala Asn Lys Asn Gly Asp Asn Gly His Lys Lys Asn Ala
785                 790                 795                 800

Gly Ile Ala Asn Phe His Val Phe Ala His Ile Asp Pro Ser Asn Arg
                805                 810                 815

Lys Leu Thr Met Leu Tyr Lys Val His Pro Gly Ala Cys Asp Gln Ser
            820                 825                 830

Phe Gly Ile His Val Ala Glu Phe Ala Asn Phe Pro Pro Ser Val Val
        835                 840                 845

Ala Leu Ala Arg Glu Lys Ala Ser Glu Leu Glu Asp Phe Ser Pro Ile
850                 855                 860

Ala Ile Ile Pro Asn Asp Ile Lys Glu Ala Ser Lys Arg Lys Arg
865                 870                 875                 880

Glu Phe Asp Arg His Asp Val Ser Arg Gly Thr Ala Arg Ala Arg Gln
                885                 890                 895

Phe Leu Gln Asp Phe Ala Gln Leu Pro Leu Asp Lys Met Asp Pro Asn
            900                 905                 910
```

Val Val Arg Gln Lys Leu Ser Lys Met Lys Thr Asp Leu Glu Arg Asp
        915                 920                 925

Ala Val Asp Ser His Trp Leu Gln Gln Phe Phe
        930                 935

<210> SEQ ID NO 5
<211> LENGTH: 160
<212> TYPE: DNA
<213> ORGANISM: Nicotiana tabacum
<220> FEATURE:
<221> NAME/KEY: unsure
<222> LOCATION: (1)..(2)
<223> OTHER INFORMATION: "n" at positions 1 and 2 can be A, C, G, or T

<400> SEQUENCE: 5
nnagagaatc ttctctagct ccccgccatt ctctttcccg ccaacccaca tccctccatt        60
ttcccattac tctataaaat cctttgcttt tcatttctac tgcagaaaag ttaaaagaaa       120
aaaaaaaatg aatgaaaatt tggaggaaca gagcaagctt                             160

<210> SEQ ID NO 6
<211> LENGTH: 163
<212> TYPE: DNA
<213> ORGANISM: Nicotiana tabacum
<220> FEATURE:
<221> NAME/KEY: unsure
<222> LOCATION: (1)..(2)
<223> OTHER INFORMATION: "n" at positions 1 and 2 can be A, C, G, or T
<221> NAME/KEY: unsure
<222> LOCATION: (141)..(141)
<223> OTHER INFORMATION: "n" at position 141 can be A, C, G, or T

<400> SEQUENCE: 6
nnaagagaat cttctctagc tccccgccat tctctttccc gccaacccac atccctccat        60
tttcccatta ctctataaaa tcctttgctt ttcatttcta ctgcagaaaa gtttaaagaa       120
aaaaaaaaat gaatgaaaat ntggaggaac agagcaagct tca                        163

<210> SEQ ID NO 7
<211> LENGTH: 163
<212> TYPE: DNA
<213> ORGANISM: Nicotiana tabacum
<220> FEATURE:
<221> NAME/KEY: unsure
<222> LOCATION: (1)..(2)
<223> OTHER INFORMATION: "n" at positions 1 and 2 can be A, C, G, or T

<400> SEQUENCE: 7
nnagagaatc ttctctagct ccccgccatt ctctttcccg ccaacccaca tccctccgtt        60
ttcccattac tctataaaat cctttgcttt tcatttctac tgcagaaaag ttaaaagaaa       120
aaaaaaaaaa tgaatgaaaa tttggaggaa cagagcaagc ttc                        163

<210> SEQ ID NO 8
<211> LENGTH: 165
<212> TYPE: DNA
<213> ORGANISM: Nicotiana tabacum
<220> FEATURE:
<221> NAME/KEY: unsure
<222> LOCATION: (1)..(2)
<223> OTHER INFORMATION: "n" at positions 1 and 2 can be A, C, G, or T
<221> NAME/KEY: unsure
<222> LOCATION: (161)..(161)
<223> OTHER INFORMATION: "n" at position 161 can be A, C, G, or T

<400> SEQUENCE: 8

```
nnttctctag ctccccgcca ttctctttcc cgccaatcca aatccctcca ttttcctcta      60
ttttcccatt actctataaa atcctttcct tttcatttct acagcataaa ggttaaagaa     120
aaaaaaatga atgaaaattt ggaggaacag agcaagttca ncgaa                     165
```

<210> SEQ ID NO 9
<211> LENGTH: 166
<212> TYPE: DNA
<213> ORGANISM: Nicotiana tabacum
<220> FEATURE:
<221> NAME/KEY: unsure
<222> LOCATION: (165)..(166)
<223> OTHER INFORMATION: "n" at positions 165 abd 166 can be A, C, G, or T

<400> SEQUENCE: 9

```
agagaatctt ctctagctcc ccgccattct ctttcccgcc aatccaagtc cctccatttt      60
cctctatttt cccattactc tataaaatcc tttccttttc atttctacag cataaaggtt     120
aaagaaaaaa aaatgaatga aaatttggag gaacagagca agctnn                    166
```

<210> SEQ ID NO 10
<211> LENGTH: 166
<212> TYPE: DNA
<213> ORGANISM: Nicotiana tabacum
<220> FEATURE:
<221> NAME/KEY: unsure
<222> LOCATION: (1)..(2)
<223> OTHER INFORMATION: "n" at positions 1 and 2 can be A, C, G, or T

<400> SEQUENCE: 10

```
nnagagaatc ttctctagct ccccgccatt ctctttcccg ccaacccaca tccctccatt      60
ttcccattac tctataaaat cctttgcttt tcatttctac tgcagaaaag ttaaaagaaa     120
aaaaaaaatg aatgaaaatt tggaggaaca gagcaagctt caatcg                    166
```

<210> SEQ ID NO 11
<211> LENGTH: 166
<212> TYPE: DNA
<213> ORGANISM: Nicotiana tabacum
<220> FEATURE:
<221> NAME/KEY: unsure
<222> LOCATION: (1)..(2)
<223> OTHER INFORMATION: "n" at positions 1 and 2 can be A, C, G, or T
<221> NAME/KEY: unsure
<222> LOCATION: (157)..(158)
<223> OTHER INFORMATION: "n" at positions 157 and 158 can be A, C, G, or T

<400> SEQUENCE: 11

```
nnagagaatc ttctctagct ccccgccatt ctctttcccg ccaacccaca tccctccatt      60
ttcccattac tctataaaat cctttgcttt tcatttctac tgcagaaaag ttaaaagaaa     120
aaaaaaaatg aatgaaaatt tggaggaaca gagcaanntt caatcg                    166
```

<210> SEQ ID NO 12
<211> LENGTH: 165
<212> TYPE: DNA
<213> ORGANISM: Nicotiana tabacum
<220> FEATURE:
<221> NAME/KEY: unsure
<222> LOCATION: (1)..(2)
<223> OTHER INFORMATION: "n" at positions 1 and 2 can be A, C, G, or T

<400> SEQUENCE: 12

```
nnagagaatc ttctctagct ccccgccatt ctctttcccg ccaacccaca tccctccatt      60
```

```
ttcccattac tctataaaat cctttgcttt tcatttctac tgcagaaaag ttaaagaaa    120 aaaaaatgaa tgaaatttg gaggaacaga gcaagcttca atcga                  165
```

<210> SEQ ID NO 13
<211> LENGTH: 314
<212> TYPE: DNA
<213> ORGANISM: Nicotiana tabacum
<220> FEATURE:
<221> NAME/KEY: unsure
<222> LOCATION: (222)..(222)
<223> OTHER INFORMATION: "n" at position 222 can be A, C, G, or T

<400> SEQUENCE: 13

```
gatatcacta gtgattcttt gcaatgaaag ttgcatcatc tccatgagca gtataatagt    60
cccgacgatc aaagaggcga actgccctag ggtccttggg tagggttttg aaaaatgaga   120
gaaatccttg agcttgctta gcatcaagtt taagctcagg aagcttgctc tgttcctcca   180
aaatcgaatt cccgcggccg ccatggcggc cgggagcatg cnacgtcggg cccaattcgc   240
cctatagtga gtcgtattac aattcactgg ccgtcgtttt acaacgtcgt gactgggaaa   300
accctggcgt tacc                                                     314
```

<210> SEQ ID NO 14
<211> LENGTH: 314
<212> TYPE: DNA
<213> ORGANISM: Nicotiana tabacum

<400> SEQUENCE: 14

```
gatatcacta gtgattcttt gcaatgaaag ttgcatcatc tccatgagca gtataatagt    60
cccgacgatc aaagaggcga actgccctag ggtccttggg cagggttttg aagaatgaga   120
gaaatccttg agcttgctta gcatccagtt taagctcggg aagcttgctc tgttcctcca   180
aaatcgaatt cccgcggccg ccatggcggc cgggagcatg ccgacgtcgg gcccaattcg   240
ccctatagtg agtcgtatta caattcactg gccgtcgttt acaacgtcg tgactgggaa   300 aaccctggcg ttac                                                     314
```

<210> SEQ ID NO 15
<211> LENGTH: 311
<212> TYPE: DNA
<213> ORGANISM: Nicotiana tabacum

<400> SEQUENCE: 15

```
atatcactag tgattctttg caatgaaagt tgcatcatct ccatgagatg tataatagtc    60
ccgacgatca aagaggcgaa ctgccctagg gtccttgggc agggttttga agaatgagag   120
aaatccttga gcttgcttag catccagttt aagctcggga agcttgctct gttcctccaa   180
aatcgaattc ccgcggccgc catggcggcc gggagcatgc gacgtcgggc ccaattcgcc   240
ctatagtgag tcgtattaca attcactggc cgtcgtttta caacgtcgtg actgggaaaa   300
ccctggcgtt a                                                        311
```

<210> SEQ ID NO 16
<211> LENGTH: 214
<212> TYPE: DNA
<213> ORGANISM: Nicotiana tabacum

<400> SEQUENCE: 16

```
gttaaaccct aattcgttaa atgttttatt acattttcag aagtttattc ttacaagtct    60
tttctagctc taattttta ttatttactt tttctcttca tattatttat tgtgtttaat   120
```

```
aaatagaggg ttcatattag ttgttcagct gatttaggga tttaaccgta gtttgattga       180
ttgaaatttg ttaccgtgaa tggttttgtt ttag                                   214

<210> SEQ ID NO 17
<211> LENGTH: 223
<212> TYPE: DNA
<213> ORGANISM: Nicotiana tabacum

<400> SEQUENCE: 17
gtaaaaccct aattctttga atgttttatt acattctcag aagtttattc ttacaagctt        60
ttttctagtt ctaatttttt ttattttata gttttttctct ttatattgtt tactgtgttt     120
aataaatgga tattgatggt tcatattagc ggttcaactg atttggggat ttaactgtag      180
tttgattgat tgatatttgt tattgtgaat ggtcttgttt tag                         223

<210> SEQ ID NO 18
<211> LENGTH: 222
<212> TYPE: DNA
<213> ORGANISM: Nicotiana tabacum

<400> SEQUENCE: 18
gtaaaaccct aattctttga atgttttatt acattctcag aagtttattc ttacaagctt        60
ttttctagtt ctaatttttt ttattttata gttttttctct ttatattgtt tactgtgttt     120
aataaatgga tattgatggt tcatattagc ggttcaactg atttggggat ttaactgtag      180
tttgattgat gatatttgtt attgtgaatg gttttgtttt ag                          222

<210> SEQ ID NO 19
<211> LENGTH: 107
<212> TYPE: DNA
<213> ORGANISM: Nicotiana tabacum

<400> SEQUENCE: 19
gtaacttttt catattattc attctgttta aatagttatt gcaccttcac ttgtagagaa        60
aattgctcgg cggttcactt aatagagaac ttttgatttt tttgcag                    107

<210> SEQ ID NO 20
<211> LENGTH: 105
<212> TYPE: DNA
<213> ORGANISM: Nicotiana tabacum

<400> SEQUENCE: 20
gtaacttttt catattattc attctgttta aatagttatt gcaccttcac ttgtagagaa        60
aattgttagt cgggttgctt aatagagaac tcttttttttt tgcag                     105

<210> SEQ ID NO 21
<211> LENGTH: 106
<212> TYPE: DNA
<213> ORGANISM: Nicotiana tabacum
<220> FEATURE:
<221> NAME/KEY: unsure
<222> LOCATION: (11)..(16)
<223> OTHER INFORMATION: "n" at positions 11-16 can be A, C, G, or T

<400> SEQUENCE: 21
gtaaactttt nnnnnnattc attctgttca aacggttatt gcaccttcac ttgtagagaa        60
aattgttagt cggtttgctt aatagagaac tcttttttttt ttgcag                    106

<210> SEQ ID NO 22
```

-continued

```
<211> LENGTH: 5
<212> TYPE: PRT
<213> ORGANISM: MutS consensus sequence

<400> SEQUENCE: 22

Thr Gly Pro Asn Met
1               5

<210> SEQ ID NO 23
<211> LENGTH: 5
<212> TYPE: PRT
<213> ORGANISM: MutS consensus sequence

<400> SEQUENCE: 23

Phe Ala Thr His Tyr
1               5

<210> SEQ ID NO 24
<211> LENGTH: 20
<212> TYPE: DNA
<213> ORGANISM: oligonucleotide primer

<400> SEQUENCE: 24
gtaacagggc ctaacatggg                                              20

<210> SEQ ID NO 25
<211> LENGTH: 19
<212> TYPE: DNA
<213> ORGANISM: oligonucleotide primer

<400> SEQUENCE: 25
ggaagtgagt agcaaacag                                               19

<210> SEQ ID NO 26
<211> LENGTH: 19
<212> TYPE: DNA
<213> ORGANISM: oligonucleotide primer

<400> SEQUENCE: 26
caggccctaa catgggtgg                                               19

<210> SEQ ID NO 27
<211> LENGTH: 20
<212> TYPE: DNA
<213> ORGANISM: oligonucleotide primer

<400> SEQUENCE: 27
aatgaaatgc aagattctcc                                              20

<210> SEQ ID NO 28
<211> LENGTH: 20
<212> TYPE: DNA
<213> ORGANISM: oligonucleotide primer

<400> SEQUENCE: 28
gaagcttgct ctgttcctcc                                              20

<210> SEQ ID NO 29
<211> LENGTH: 17
<212> TYPE: DNA
<213> ORGANISM: oligonucleotide primer
<220> FEATURE:
<221> NAME/KEY: misc_feature
<222> LOCATION: (3)..(3)
<223> OTHER INFORMATION: "n" at position 3 can be A, C, G, or T
```

-continued

```
<221> NAME/KEY: misc_feature
<222> LOCATION: (6)..(6)
<223> OTHER INFORMATION: "n" at position 6 can be A, C, G, or T
<221> NAME/KEY: misc_feature
<222> LOCATION: (9)..(9)
<223> OTHER INFORMATION: "n" at position 9 can be A, C, G, or T

<400> SEQUENCE: 29
acnggnccna ayatggg                                                    17

<210> SEQ ID NO 30
<211> LENGTH: 17
<212> TYPE: DNA
<213> ORGANISM: oligonucleotide primer
<220> FEATURE:
<221> NAME/KEY: misc_feature
<222> LOCATION: (9)..(9)
<223> OTHER INFORMATION: "n" at position 9 can be A, C, G, or T
<221> NAME/KEY: misc_feature
<222> LOCATION: (12)..(12)
<223> OTHER INFORMATION: "n" at position 12 can be A, C, G, or T

<400> SEQUENCE: 30
tgyaartgng tncgraa                                                    17

<210> SEQ ID NO 31
<211> LENGTH: 19
<212> TYPE: DNA
<213> ORGANISM: oligonucleotide primer

<400> SEQUENCE: 31
caggccctaa catgggtgg                                                  19

<210> SEQ ID NO 32
<211> LENGTH: 6
<212> TYPE: PRT
<213> ORGANISM: MSH2 consensus sequence

<400> SEQUENCE: 32

Asp Tyr Tyr Thr Ala His
1               5

<210> SEQ ID NO 33
<211> LENGTH: 20
<212> TYPE: DNA
<213> ORGANISM: oligonucleotide primer

<400> SEQUENCE: 33
gattattata cagctcatgg                                                 20

<210> SEQ ID NO 34
<211> LENGTH: 6
<212> TYPE: PRT
<213> ORGANISM: MSH2 consensus sequence

<400> SEQUENCE: 34

Met Trp Leu Lys Gln Pro
1               5

<210> SEQ ID NO 35
<211> LENGTH: 17
<212> TYPE: DNA
<213> ORGANISM: oligonucleotide primer

<400> SEQUENCE: 35
atgtggctga aacaacc                                                    17
```

```
<210> SEQ ID NO 36
<211> LENGTH: 22
<212> TYPE: DNA
<213> ORGANISM: oligonucleotide primer

<400> SEQUENCE: 36
cttatgtcca ttgtctccat tc                                              22

<210> SEQ ID NO 37
<211> LENGTH: 20
<212> TYPE: DNA
<213> ORGANISM: oligonucleotide primer

<400> SEQUENCE: 37
gtccattgtc tccattcttg                                                 20

<210> SEQ ID NO 38
<211> LENGTH: 20
<212> TYPE: DNA
<213> ORGANISM: oligonucleotide primer

<400> SEQUENCE: 38
gcaccccaaa gcgcctgatg                                                 20

<210> SEQ ID NO 39
<211> LENGTH: 23
<212> TYPE: DNA
<213> ORGANISM: oligonucleotide primer

<400> SEQUENCE: 39
ctgatgcaca ttcgaaccca gag                                             23

<210> SEQ ID NO 40
<211> LENGTH: 22
<212> TYPE: DNA
<213> ORGANISM: oligonucleotide primer

<400> SEQUENCE: 40
acatatagtt caagagtacg gt                                              22

<210> SEQ ID NO 41
<211> LENGTH: 22
<212> TYPE: DNA
<213> ORGANISM: oligonucleotide primer

<400> SEQUENCE: 41
gctattgttt caaacatgtt tc                                              22

<210> SEQ ID NO 42
<211> LENGTH: 22
<212> TYPE: DNA
<213> ORGANISM: oligonucleotide primer

<400> SEQUENCE: 42
ttggaggaac agagcaagct tc                                              22
```

PLANT MSH2 SEQUENCES AND METHODS OF USE

FIELD OF THE INVENTION

The invention relates to the genetic manipulation of plants, particularly to modulating recombination and DNA repair mechanisms in plants.

BACKGROUND OF THE INVENTION

Mismatched base pairing in DNA duplexes may arise due to errors introduced during DNA replication (Echols and Goodman (1991) *Annu. Rev. Biochem.* 60:477–511; Kornberg and Baker (1991) *DNA replication*, W. H. Freeman & Co., New York), heteroduplex formation during homologous recombination (Holliday (1964) *Genet Res.* 5:282–304; Petes and Hill (1988) *Annu. Rev. Genet.* 22:147–168), as a consequence of mutation and by enzymatic modification of DNA such as deamination of 5-methylcytosine. Such mismatches can lead to genome instability. Therefore, all living systems have evolved specialized pathways to repair specific mismatches which are somewhat different than other DNA repair mechanisms such as base excision repair and nucleotide excision repair (Wildenberg and Messelson (1975) *Proc. Natl. Acad. Sci. USA* 72:2202–2206; Wagner and Messelson (1996) *Proc. Natl. Acad. Sci. USA* 73:4136–4139; Radman and Wagner (1986) *Annu. Rev. Genet.* 20:523–538; Freidberg (1985) *DNA Repair*, W. H. Freeman & Co., New York). Early studies in prokaryotic systems, especially *Escherichia coli*, led to the identification of one of these pathways, called the long-patch repair system or the methyl-directed mismatch-repair system (Radman and Wagner (1986) *Annu. Rev. Genet.* 20:523–538). This pathway exhibits rather broad specificities for repairing mismatches generated during DNA biosynthesis as well as recombination. Several genes essential for the methyl-directed mismatch repair have been identified in *E. Coli*. Primary among these are mutS, mutL, mutH, UvrD, and the Dam methyltransferase and exonuclease genes (Freidberg (1985) *DNA Repair*, W. H. Freeman & Co., New York).

Genetic evidence for the existence of the mismatch-repair pathways in eukaryotes has been around since the late 1960s (Emerson (1969) *Genetic Organization* Caspari & Ravin, eds., Academic Press, New York, pp. 267–360). However, it was not until the early 1990s, following the first biochemical evidence for the repair activity in a eukaryote (Muster-Nassal and Kolodner (1986) *Proc. Natl Acad. Sci. USA* 83:7618–7622) and the isolation and characterization of yeast mutS homologues, MshI (Reenan and Kolodner (1992) *Genetics* 132:963–973), MSH2 (Reenan and Kolodner (1992) *Genetics* 132:975–985) and Msh3 (New et al. (1993) *Mol. Gen. Genet.* 239:97–108), that the existence of a mismatch-repair pathways in eukaryotes was clearly established. Subsequently, several eukaryotic Msh genes have been cloned and characterized (Nickoloff and Hoeskstra (1998) *DNA Damage and Repair*, vols. I–II, Humana Press, New York). Extensive and careful biochemical studies over the past decade have revealed that the gene products (denoted by MSH1, MSH2 etc.) of individual Msh gene family members exhibit remarkable specificity in their ability to participate in different biological processes. Thus, in yeast, MSH1 is primarily responsible for mitochondrial DNA repair, MSH2, MSH3, and MSH6 are involved in base mismatch repair and in modulating recombination, whereas MSH4 and MSH5 and are involved in modulating recombination. Precisely how MSH2, MSH3, and MSH6 participate in recombination has not yet been determined. It has been proposed that in addition to their mismatch-repair activity, these gene products interact with other cellular components involved in resolution of the Holliday junction (Nickoloff and Hoeskstra (1998) *DNA Damage and Repair*, vols. I–II, Humana Press, New York).

Interestingly, in a recent study with mammalian cells, mismatch repair has been shown to have an anti-recombinational effect. Thus, in a mouse msh2 cell line, target integration of a plasmid DNA at the Rb locus was increased 50-fold. Furthermore, MSH2 and Msh3 homologues are known to be involved in gene targeting and gene modification processes (deWind et al. (1995) *Cell* 82:321–330). The deWind reference, as well as the Abuin et al. ((2000) *Cellular Biol* 20:149–157), disclose that MSH2 deficiency increases the recombination frequency between non-identical DNA substrates. The anti-recombination effect is only observed with non-identical DNAs; recombination between identical DNA substrates is unaffected in msh2 lines. This is likely because pairing of homologous DNA sequences does not lead to DNA mismatches.

A combination of factors appears to render plant genomes highly susceptible to mutation. Complex genomes of higher plants contain large numbers of putative mutational hotspots, such as microsatellites, repeated elements and 5-methylcytosine. In addition, unlike many other multicellular organisms, plant germ cells are derived from somatic progenitors that have undergone many cell divisions. High DNA replication fidelity is crucial to the faithful transmission of genetic information to subsequent plant generations. The DNA mismatch-repair system plays a crucial role in maintaining the integrity of the genome. Mismatch-repair activities identify and catalyze the repair of DNA polymerase errors and base-pair mismatches and act to restrict recombination between non-homologous DNA sequences. The proofreading and anti-recombination functions of mismatch-repair activities likely play a key role in the fitness of subsequent plant generations.

The methyl-directed mismatch-repair system of *E. coli* is well characterized. For review, see Modrich and Lahue ((1996) *Annu. Rev. Biochem.* 65:101–133). In brief, the key components in *E. coli* mismatch repair are: MutS, which interacts directly with mismatched DNA; and MutL, which, through its interaction with MutS, activates the MutH endonuclease. Upon activation, MutH endonuclease introduces a nick in the unmethylated DNA flanking the site of the base-pair mismatch at a hemi-methylated GATC site. The nicked strand is then degraded through the site of the mismatch and the degraded sequences are resynthesized and ligated.

Eukaryotes encode a family of MutS orthologs or homologs, known as Msh. Mismatch recognition in eukaryotes is accomplished by a heterodimer of MSH proteins, depending upon the type of mismatch. Heterodimers of MSH2 and MSH3 recognize insertion mismtaches and DNA loops, while heterodimers of MSH2 and MSH6 interact preferentially with base-pair mismatches and single base insertions. (Marsischky et al. (1996) *Genes Devel.* 10:407–420) MSH2 is the key component in mismatch recognition, because it is required to initiate correction of any sort of mismatch. Biochemical and genetic studies in *E. coli* have demonstrated an antirecombination activity associated with homologs of MutS (Rayssiguier et al. (1989) *Nature* 342:396–401). The role of MSH2 in preventing recombination between partially homologous (homeologous) sequences has also been established in *S. cerevisiae* (Alani et al. (1994) *Genetics.* 137:19–39).

While much is known about the biochemical nature of DNA mismatch repair in bacterial, yeast, and mammalian systems, very little is known about the corresponding repair pathways in plants. MutS homolog genes have been identified in a number of plant species, including *Arabidopsis*, maize and wheat, but the contributions of these proteins to genome stability and DNA proofreading has not been established.

SUMMARY OF THE INVENTION

Compositions and methods for altering mismatch repair and recombination frequency are provided. Such compositions and methods find use in altering mutation rates, recombination frequencies and DNA repair processes, in producing dominant-negative MSH2 polynucleotides and the polypeptides encoded thereby, and in improving the efficiency of transformation and chimeraplasty, in both eukaryotic and prokaryotic organisms. The compositions comprise isolated nucleic acid molecules comprising nucleotide sequences encoding tobacco MSH2 proteins, nucleotide sequences that encode dominant-negative MSH2 variants, and the proteins encoded by such nucleotide sequences. Further provided are expression cassettes comprising an MSH2 nucleotide sequence of the invention operably linked to a promoter that drives expression in an organism of interest. The methods involve introducing into an organism an MSH2 nucleotide sequence of the invention operably linked to a promoter that drives expression in the organism or alternatively introducing an MSH2 protein into the organism. If decreased expression is desired, the methods can additionally involve co-suppression, antisense suppression, or a dominant-negative approach.

Additionally provided are nucleic acid molecules sequences comprising nucleotide sequences of promoters of tobacco MSH2 genes. Expression cassettes comprising such MSH2 promoter sequences are also provided. The promoter nucleotide sequences of the invention find use in methods for regulating the expression of a heterologous nucleotide sequence of interest in a plant. The methods involve introducing in the genome of a plant a nucleotide construct comprising an MSH2 promoter nucleotide sequence operably linked to a heterologous sequence.

Transformed host cells, transformed plants, tissues, cells and seeds thereof are provided.

BRIEF DESCRIPTION OF THE DRAWINGS

FIG. 1 summarizes the nucleotide polymorphisms identified in NtMSH2 (*Nicotiana tabacum* MSH2) cDNA and genomic sequences. Degenerate polymorphisms are present at nucleotide positions 36, 48, 81, 93 and 144 with respect to the translational start. The nucleotide polymorphism at position 145 is non-degenerate. NtMSH2A1, NtMSH2A2 and NtMSH2A3 encode serine, while NtMSH2B1 encodes alanine. Single letter amino acid abbreviations are used.

DETAILED DESCRIPTION OF THE INVENTION

The invention is drawn to the processes that living organisms use to maintain the fidelity of DNA during replication and recombination. In particular, the invention provides isolated nucleic acid molecules comprising nucleotide sequences which encode MutS homologues (MSH) from tobacco, particularly MSH2, and the isolated proteins encoded by such nucleotide sequences. Such nucleotide sequences find use in plants and other organisms in altering the frequency of recombination and the efficiency of gene modification processes such as, for example, chimeraplasty. The invention further provides isolated nucleotide molecules comprising promoters of the tobacco MSH2 genes. Such promoters find use in regulating gene expression in plants.

Compositions of the invention include nucleotide sequences from genes that encode proteins known as MSH2 proteins. Such proteins are known to be involved in the processes of DNA repair and recombination. In particular, the present invention provides for isolated nucleic acid molecules comprising nucleotide sequences encoding the amino acid sequences shown in SEQ ID NOs: 2 and 4, or the nucleotide sequences encoding the DNA sequences deposited in a bacterial host as Patent Deposit Nos. PTA-1889 and PTA-1890. Further provided are polypeptides having an amino acid sequence encoded by a nucleic acid molecule described herein, for example those set forth in SEQ ID NOs: 1 and 3 those deposited in a bacterial host as Patent Deposit Nos. PTA-1889 and PTA-1890, and fragments and variants thereof.

Plasmids containing the nucleotide sequences (SEQ ID NOS:1 and 3) of the invention were deposited with the Patent Depository of the American Type Culture Collection (ATCC), 10801 University Blvd., Manassas, Va., on May 18, 2000 and assigned Patent Deposit Nos. PTA-1889 and PTA-1890. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence mismatch-repair activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of an MSH2 nucleotide sequence that encodes a biologically active portion of an MSH2 protein of the invention will encode at least 15, 25, 30, 50, 100, 150, 200, 250, 300, 350, 400, 450, 500, 550, 600, 650, 700, 750, 800, 850, or 900 contiguous amino acids, or up to the total number of amino acids present in a full-length MSH2 protein of the invention (for example, 939 amino acids for each of SEQ ID NOS:2 and 4, respectively). Fragments of an MSH2 nucleotide sequence that are useful as hybridization probes or PCR primers generally need not encode a biologically active portion of an MSH2 protein.

Thus, a fragment of an MSH2 nucleotide sequence may encode a biologically active portion of an MSH2 protein, or it may be a fragment that can be used as a hybridization probe or PCR primer using methods disclosed below. A biologically active portion of an MSH2 protein can be prepared by isolating a portion of one of the MSH2 nucleotide sequences of the invention, expressing the encoded portion of the MSH2 protein (e.g., by recombinant expression in vitro), and assessing the activity of the encoded portion of the MSH2 protein. Nucleic acid molecules that are fragments of an Msh nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,750, 2,000, 2,250, 2,500, 2,750, or 3,000 nucleotides, or up to the number of nucleotides present in a full-length MSH2 nucleotide sequence disclosed herein (for example, 3033 nucleotides for each of SEQ ID NOS: 1 and 3).

Similarly, a fragment of an MSH2 nucleotide sequence may encode a biologically active portion of a promoter that is capable of driving the expression of an operably linked nucleotide sequence in a plant or it may be a fragment that can be used as a hybridization probe or PCR primer using methods disclosed below. A biologically active portion of an Msh2 promoter can be prepared by isolating a portion of one of the MSH2 promoter sequences of the invention, operably linking the promoter sequence to a nucleotide sequence such as, for example, a reporter gene, transforming a plant cell with the operably linked construct, and assessing the activity of the MSH2 promoter in the plant cell. Nucleic acid molecules that are fragments of an MSH2 nucleotide sequence comprise at least 16, 20, 50, 75, 100, 150, or 160 nucleotides, or up to the number of nucleotides present in a full-length MSH2 promoter sequence disclosed herein (for example, 160, 163, 163, 165, 166, 166, 166, 165, nucleotides for SEQ ID NOS: 5, 6, 7, 8, 9, 10, 11, and 12, respectively).

By "variants" is intended substantially similar sequences. For nucleotide sequences, conservative variants include those sequences that, because of the degeneracy of the genetic code, encode the amino acid sequence of one of the MSH2 polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an MSH2 protein of the invention, or in the case of promoter sequences, retain the capability of driving the expression of an operably linked nucleotide sequence in a plant. Generally, variants of a particular nucleotide sequence of the invention will have at least about 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, mismatch-repair activity as described herein. Such variants may result from, for example, genetic polymorphism or from human manipulation. Biologically active variants of a native MSH2 protein of the invention will have at least about 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the MSH2 proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired MSH2 activity, the mutations that will be made in the DNA encoding the variant must not place the sequence out of reading frame and preferably will not create complementary regions that could produce secondary mRNA structure. See, EP Patent Application Publication No. 75,444.

Additionally, the proteins of the invention also encompass fragments and variants that can be in dominant-negative strategies for reducing the biological activity of a MutS homologue or MSH2. Such dominant-negative fragments and variants of the MSH2 proteins of the invention, when expressed in a cell, are capable of reducing the biological activity of a MutS homologue or MSH2 therein. It is recognized that such dominant-negative variants can be full-length MSH2 proteins or can be truncated forms. The invention also encompasses the nucleotide sequences which encode these dominant-negative fragments and variants The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by one or methods known in the art including, but not limited to, gel shift assays to demonstrate binding to specific mismatched substrates, in vitro mismatch repair assays, and in vivo mismatch repair assays, such as, for example, determination of in vivo microsatellite stability and monitoring spontaneous mutation rates. See, for example, Marsischky et al. (1996) *Genes Devel.* 10:407–420; deWind et al. (1995) *Cell* 82:321–330; Holmes et al. (1990) *Proc. Natl. Acad. Sci USA* 87:5837–5841; Reenan and Kolodner (1992) *Genetics* 132:963–973 See, Su et al. (1988) *J. Biol. Chem.* 263:6829–6835; Holmes et al. (1990) *Proc. Natl. Acad. Sci. USA* 87:5837–5841; and Rice et al. (2000) *Plant Physiol.* 123:427–438; all of which are hereby herein incorporated by reference.

Variant nucleotide sequences and proteins also encompass sequences and proteins derived from a mutagenic and/or recombinogenic procedure such as DNA shuffling. With such a procedure, one or more different MSH2 coding sequences can be manipulated to create a new MSH2 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Msh gene of the invention and other known Msh genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire MSH2 sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the MSH2 sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire MSH2 sequence disclosed herein, or one or more portions thereof, may be used as a probe capable of specifically hybridizing to corresponding MSH2 sequences and messenger RNAs. To achieve specific hybridization under a variety of conditions, such probes include sequences that are unique among MSH2 sequences and are preferably at least about 10 nucleotides in length, and most preferably at least about 20 nucleotides in length. Such probes may be used to amplify corresponding MSH2 sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1 ° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode of an MSH2 protein and which hybridize under stringent conditions to the MSH2 sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide or polypeptide sequence, wherein the polynucleotide or polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100, or longer. Those of skill in the art understand that to avoid a high similarity to a reference sequence due to inclusion of gaps in the polynucleotide or polypeptide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 10 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et. al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates a global alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 for polypeptides and NWSEAP-DNA for polynucleotides (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The MSH2 nucleotide sequences find use in methods for altering DNA repair processes in plants and other organisms. MSH2 is known to be involved in mismatch-repair systems of organisms. Furthermore, organisms harboring mutant alleles of msh2 display increased levels of recombination relative to wild-type organisms (deWind et al. (1995) *Cell* 82:321–330). While the present invention does not depend on a particular mechanism, it is believed that MSH2 facilitates mismatch repair through direct interactions with several other proteins, including, but not limited to, MSH3 and MSH6. To alter mismatch repair in an organism, the organism can be transformed with an MSH2 nucleotide sequence of the invention, or a fragment or variant thereof.

An alteration in mismatch repair in an organism can comprise at least one of change in the DNA of an organism, or at least one cell thereof. Such changes include, but are not limited to, substitutions, additions, deletions, inversions, and other rearrangements. Typically, such an alteration in mismatch repair can be determined by monitoring mutation frequency. Methods, for monitoring mutation frequency are known in the art and typically involve determining whether a change has occurred in the DNA sequence of one or more genes by monitoring loss, or gain, of a particular function associated with a particular product encoded by the gene. Other methods can be employed, however, to ascertain mutation frequency at the nucleic acid level including, but not limited to, RFLP analysis, PCR, and DNA sequencing. Typically, mutation frequency is assessed by comparing the mutation frequency of an organism that is modified according to the methods of the present invention to a control organism or similar unmodified organism.

The methods of the invention additionally find use in altering recombination frequency in plants and other organisms. By expressing an MSH2 nucleotide sequence of the invention in a plant or other organism, recombination efficiency can be altered. While the invention does not depend on a particular biological mechanism, MSH2 is believed to be involved in the resolution of the Holliday junction that occurs during genetic recombination in vivo. Decreasing the level or activity of MSH2 in an organism is expected to increase the integration of exogenous DNA through homologous or homeologous recombination into specific targets within the genome. hi a mouse msh2 cell line, target integration of plasmid DNA at the Rb locus was increased about fifty-fold (deWind et al. (1995) *Cell* 82:321–330). Thus, the MSH2 nucleotide sequences can be used to increase integration of foreign DNA into target genes within the genome. Furthermore, the MSH2 nucleotide sequences can be employed to increase the efficiency of methods of in vivo genetic modification. Such methods are believed to involve recombination, and include, for example, chimeraplasty and gene replacement.

By "exogenous DNA" is intended any nucleic acid molecule that is introduced into a cell. It is recognized that the invention also encompasses nucleic acid molecules comprised of deoxyribonucleotides, ribonucleotides, and combination thereof. Such deoxyribonucleotides and ribonucleotides include, but not limited to, naturally occurring and synthetic form, and derivatives thereof.

By lowering the level or activity of MSH2 in a plant or other organism, the efficiency of chimeraplasty or gene replacement can be increased. By "efficiency of chimeraplasty" or "efficiency of gene replacement" is intended the proportion of cells or organisms having the desired genetic modification recovered from the total number of cells or organisms used in a chimeraplasty or gene replacement attempt, respectively.

The methods of the invention additionally encompass the use of dominant-negative strategies to reduce a particular biological activity of a MutS homologue or MSH2 within an organism. Such strategies involve the expression in an organism of an MSH2 nucleotide sequence of the invention, or fragment thereof that encodes a portion of the MSH2. The methods of the invention additionally encompass nucleotide sequences encoding variants of the MSH2 proteins of the invention, and fragments thereof, that can be used in dominant-negative strategies to reduce the biological activity of a MutS homologue or MSH2 within an organism or cell thereof. Such dominant-negative strategies are known in the art and can involve the expression of a modified subunit of a multisubunit protein. See, for example, Alani et al. (1997) *Mol Cell Biol.* 17:2436–244; Drotschmann et al. (1999) *Proc. Natl. Acad. Sci. USA* 96:2970–2975; and Wu and Marinus (1994) *J. Bact.* 176:5393–5400; all of which are hereby herein incorporated by reference. Generally, such a modified subunit comprises a polypeptide that is able to affect, or interact with, other members of the multisubunit protein complex and thereby reduce, or eliminate, the biological activity of the complex. While the methods of the invention do not depend a particular biological mechanism, typically such a dominant-negative approach will involve the expression of a variant of a MSH2 protein of the invention that does not possess the complete biological activity of the native protein. It is recognized that such an dominant-negative approach does not depend on eliminating or reducing the expression of native MSH2 genes in a plant, only that such an approach involves the expression of a variant of an MSH2 of the invention that is capable of causing a dominant-negative phenotype.

By "dominant-negative phenotype" is intended a phenotype that, when compared to a wild type phenotype or a previous phenotype of the organism, is substantially altered in a negative manner including, but not limited to, a loss or reduction in a particularly cellular function such as, for example, an enzyme activity or mismatch repair. Further it is recognized that, while the methods of the invention can be used to negatively affect, through a dominant-negative approach, the cellular activity of an MSH2 protein, or complex thereof, desired phenotypic changes can result in a organism including, but not limited to, an increase in recombination, an improvement in transformation efficiency and an increase in the efficiency of chimeraplasty.

In an embodiment of the invention, a nucleotide construct comprising an MSH2 sequence of the invention, or variant or fragment thereof, is introduced into an organism or host cell, particularly a bacterial cell, more particularly an *E. coli* cell. DNA repair is then monitored in the transformed organism, or host cell, by, for example, determining the mutation rate. Such transformed organisms and host cells find use in producing MSH2 nucleotide sequences that can be used in dominant-negative strategies to disrupt DNA repair processes in bacteria, plants, and other organisms. Such desired MSH2 nucleotide sequences encode dominant-negative MSH2 variants. By "dominant-negative MSH2 variant" is intended a polypeptide that is capable of conferring a dominant-negative phenotype on a host cell. In particular, the dominant-negative phenotype will impair DNA repair in a host cell or organism. Such an impairment in DNA repair can cause an increase in the mutation rate and/or recombination frequency in a host cell or organism. Thus, the desired MSH2 nucleotide sequence, which encodes a dominant-negative MSH2 variant, can be identified by, for example, selecting a host cell with impaired DNA repair as detected by an increase in the mutation rate and/or recombination frequency therein. Such desired MSH2 nucleotide sequences and the dominant-negative MSH2 variants encoded thereby find use in methods for altering DNA repair processes, particularly methods for increasing the mutation and/or recombination rates in an organism.

Thus, the invention provides methods for identifying MSH2 nucleotide sequences which encode dominant-negative MSH2 variants that are capable of conferring a dominant-negative phenotype on a cell. The invention further provides isolated MSH2 nucleotide sequences encoding such MSH2 variants, the dominant-negative MSH2 variants encoded thereby, and host cells and organisms transformed with such MSH2 nucleotide sequences. Such transformed host cells and organisms include, but are not limited to, bacteria, yeast, fungi, animals and plants.

The dominant-negative MSH2 variant of the invention involve the use of an MSH2 amino acid sequence having at least one amino acid substitution, truncation, internal deletion or insertion. Any MSH2 nucleotide sequence and any MSH2 amino acid sequence known the art can be used in the methods of the present invention. Such MSH2 nucleotide sequences and amino acid sequences include, but are not limited to, GenBank Accession Nos. AF109243, AF003005, AF002706, AF026549, U87911, and M84170. At least one substitution, truncation, internal deletion or insertion can be introduced in the amino acid sequence of an MSH2 protein by, for example, modifying the nucleotide sequence that encodes the MSH2 protein using methods known in the art. The modified MSH2 nucleotide sequence can then be introduced into an organism or host cell according to the methods of the present invention.

For expression in *E. coli,* the expression cassette can additionally comprise an operably linked promoter. Preferably, such a promoter drives high level gene expression in *E. coli*, such as, for example, the T5 promoter. The expression cassette can further comprise a nucleotide sequence that encodes an epitope or tag that can be readily detected by immunological or other known methods. Such epitopes or tags, and methods for their use, are known in the art. A nucleotide sequence encoding the epitope or tag can be operably linked to the MSH2 nucleotide sequence for the transcription of a fusion protein comprising the MSH2 amino acid sequence and the amino acid sequence of the epitope or tag. Typically, the epitope or tag is N-terminal or C-terminal relative to the MSH2 amino acid sequence. Such epitopes and tags are known in the art to be useful for the detection and/or purification of fusion proteins.

In another embodiment of the invention, methods are provided for decreasing the level or activity of an MSH2 protein of the invention in a plant or cell thereof. Plants or cells with decreased MSH2 protein or activity find use in methods for increasing recombination frequency, increasing mutation rate and increasing the efficiency of chimeraplasty. The level or activity of MSH2 can be reduced in the plant or cell by, for example, introducing into the plant or cell, a nucleotide construct comprising a promoter that drives expression in a plant operably linked to an MSH2 nucleotide sequence of the invention. The methods can additionally involve co-suppression, antisense suppression or a dominant-negative strategy to reduce or substantially eliminate the biological activity of MSH2.

Alternatively, an MSH2 nucleotide sequence of the invention that encodes an MSH2 protein that is known to cause a dominant-negative phenotype, can be directly introduced into a plant or other host cell. Such MSH2 proteins encompass the fragments and variants as discussed supra. Any method for introducing a protein into a plant or other host cell that is known in the art can be employed in the methods of the present invention. For example, a protein can be introduced into a plant by particle bombardment in a manner analogous to that used for the introduction of nucleic acids. See, U.S. Pat. No. 4,945.050. The MSH2 protein can be associated with or precipitated onto the microprojectiles or microparticles and then bombarded into plant cells. Nucleotide constructs comprising, for example, a chimeraplast or other nucleotide sequence comprising a gene of interest can also be associated with the same microprojectiles or two separate groups of microprojectiles—one with the MSH2 protein and the other with the chimeraplast or nucleotide sequence of interest—can be prepared and then co-bombarded. Alternatively, the plant cells can be bombarded separately with the MSH2-associated particles and the chimeraplast-associated or nucleotide construct-associated particles.

In another embodiment of the invention, the MSH2 protein can be produced in an *Agrobacterium* cell and delivered to a plant cell by the *Agrobacterium* cell at about the same time as the bacterial cell delivers its Ti plasmid, comprising a gene of interest, to the plant cell. To produce an MSH2 protein of the invention in *Agrobacterium*, an *Agrobacterium* cell can be transformed with an MSH2 nucleotide sequence of the invention that is operably linked to a promoter that drives expression in the bacterial cell. Methods for transforming *Agrobacterium* are known in the art and include, but are not limited to, electroporation. Promoters that drive the expression of operably linked nucleotide sequences in *Agrobacterium* are also known in the art. It is recognized that to facilitate the transfer of the MSH2 protein into a plant cell, fusion proteins comprising at least a portion of an MSH2 protein of the invention and at least a portion of one or more additional proteins such as, for example, VirF and VirE2 can be obtained by preparing a nucleotide construct comprising at least a portion of an MSH2 nucleotide sequence of the invention operable operably linked to a coding sequence for the additional protein or desired portion thereof. The construction of such fusion proteins for transfer by *Agrobacterium* to a plant cell, and methods of their use, are known to those of ordinary skill in the art. Generally, such methods involve fusing the protein of interest to the N-terminal end of a VirF, VirE2, or a transport domain thereof. The transport domains of VirF and VirE2 proteins are known to be located in the C-terminal regions of the proteins. See, Vergunst et al. ((2000) Science 290:979–982) and the references cited therein; herein incorporated by reference.

The MSH2 nucleotide sequences and proteins of the invention find further use in methods for improving transformation efficiency. By "improving transformation efficiency" is intended an increase in the recovery of transformed cells, tissues, organs, or organisms from a transformation attempt. The methods of the invention involve introducing one or more MSH2 nucleotide sequences or proteins into a host cell. Such host cells can provide improved transformation efficiency in a transformation attempt. Typically, the Msh nucleotide sequences or proteins will be introduced into a host cell prior to, or concomitantly, with a nucleotide sequence of interest to improve transformation efficiency with respect to the nucleotide sequence of interest. In particular, the methods can increase the recovery of stably transformed cells, tissues, organs, or organisms in a transformation attempt. Thus, the invention further provides improved methods for transforming organisms, particularly plants.

While invention does not depend on a particularly biological or genetic mechanism, it is recognized that altering DNA mismatch repair and DNA recombination in an organism can affect cellular processes that are involved in the stable incorporation of a nucleotide construct of interest, or at least one nucleotide thereof, into the genome of the cell. Further, it is recognized that reducing, or otherwise inhibiting, DNA mismatch repair in an organism can improve the efficiency of genetic transformation methods, such as, for example, chimeraplasty, which are believed to involve circumventing the DNA mismatch-repair system of a host cell. Similarly, is also recognized that reducing, or otherwise inhibiting, the activity or function of a protein that is known to prevent or negatively impact recombination in a cell can increase recombination in the cell. Yeast msh2 mutants have decreased mismatch repair and increased recombination, particularly recombination between partially homologous (homeologous) sequences (Alani et al. (1994) *Genetics* 137:9–39.)

In an embodiment of the invention, a plant is stably transformed with a nucleotide construct comprising an MSH2 nucleotide sequence of the invention operably linked to a promoter that drives expression in a plant cell. Such a plant finds use in methods for improving transformation efficiency. Preferably, the promoter drives expression in plant cells that are targeted for transformation with a nucleotide sequence of interest. More preferably, the promoter is a tissue-preferred or chemical-regulated promoter.

The invention additionally provides nucleotide sequences of MSH2 promoters. The MSH2 promoter nucleotide sequences of the invention find use in methods for regulating gene expression in a plant. Such methods involve operably linking an MSH2 promoter sequence of the invention to a heterologous nucleotide sequence wherein the MSH2 promoter allows the transcription of the heterologous nucleotide sequence. By "heterologous nucleotide sequence" is intended any nucleotide sequence that is not identical to that entire portion of the native MSH2 gene that immediately follows, in the 3' direction, the MSH2 promoter of the invention, as is found within the native MSH2 gene from which the promoter originates. While the invention does not depend on a particular heterologous nucleotide sequence, preferred sequences are coding sequences. The heterologous nucleotide can be operably linked in either the sense or antisense orientation depending on the desired outcome.

The MSH2 sequences of the invention are provided in expression cassettes for expression in the plant or other organism of interest. For MSH2 coding sequences, the cassette will include 5' and 3' regulatory sequences operably linked to a MSH2 sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

The expression cassettes are provided with a plurality of restriction sites for insertion of the MSH2 coding sequence to be under the transcriptional regulation of the regulatory regions. The expression cassette may additionally contain selectable marker genes.

The expression cassette will include in the 5'–3' direction of transcription, a transcriptional and translational initiation region, a MSH2 DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a "chimeric gene" comprises a coding sequence operably linked to a transcription initiation region that is heterologous to the coding sequence, or any combination of a promoter with a coding sequence that is not identical to the structure of a native, unmodified gene.

While it may be preferable to express the sequences using heterologous promoters, the native promoter sequences may be used. Such constructs would change expression levels of MSH2 in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Similarly, the MSH2 promoter sequences of the invention are provided in expression cassettes for expression in the plant of interest. The cassette will include an MSH2 promoter sequence of the invention operably linked to a coding sequence. Any coding sequence known in the art can be used. The cassette will additionally comprise 3' regulatory sequences. If necessary, the cassette can also contain additionally 5' regulatory sequences.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In1-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced MSH2 expression within a particular plant tissue. Tissue-preferred promoters include, but are not limited to, those described by Yamamoto et al. (1997) *Plant J.* 12(2) 255–265; Kawamata et al. (1997) *Plant Cell Physiol.* 38(7) :792–803; Hansen et al. (1997) *Mol. Gen Genet.* 254(3) :337–343; Russell et al. (1997) *Transgenic Res.* 6(2) :157–168; Rinehart et al. (1996) *Plant Physiol.* 112(3) :1331–1341; Van Camp et al. (1996) *Plant Physiol.* 112(2) :525–535; Canevascini et al. (1996) *Plant Physiol.* 112(2) :513–524; Yamamoto et al. (1994) *Plant Cell Physiol.* 35(5) :773–778; Lam (1994) *Results Probl. Cell Differ.* 20:181–196; Orozco et al. (1993) *Plant Mol Biol.* 23(6) :1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate amnmonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol.

78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium* -mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923–926); and Lec1 transformation (WO 00/28058). Also see Weissinger et al. (1988) *Annu. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. It is recognized that certain embodiments of the invention do not depend on the stable incorporation of the MSH2 nucleotide sequences of the invention into the genome of an organism.

Methods for introducing nucleotide constructs into plants are known in the art including, but not limited to, stable transformation methods, transient transformation methods, and virus-mediated methods. By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention can be introduced into plants by contacting plants with a virus or viral nucleic acids. Generally, such methods involve incorporating a nucleotide construct of the invention within a viral DNA or RNA molecule. It is recognized that an MSH2 of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

It is recognized that with these nucleotide sequences, antisense constructions, complementary to at least a portion of the messenger RNA (mRNA) for the MSH2 sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention can employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, can incorporate into the genome of the plant. For the present invention, alterations to the genome include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeraplasts, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774–8778; herein incorporated by reference.

The present invention may be used for transformation of any plant species, including, but not limited to, monocots and dicots. Examples of plant species of interest include, but are not limited to, corn (Zea mays), Brassica sp. (e.g., B. napus, B. rapa, B. juncea), particularly those Brassica species useful as sources of seed oil, alfalfa (Medicago sativa), rice (Oryza sativa), rye (Secale cereale), sorghum (Sorghum bicolor, Sorghum vulgare), millet (e.g., pearl millet (Pennisetum glaucum), proso millet (Panicum miliaceum), foxtail millet (Setaria italica), finger millet (Eleusine coracana)), sunflower (Helianthus annuus), safflower (Carthamus tinctorius), wheat (Triticum aestivum), soybean (Glycine max), tobacco (Nicotiana tabacum), potato (Solanum tuberosum), peanuts (Arachis hypogaea), cotton (Gossypium barbadense, Gossypium hirsutum), sweet potato (Ipomoea batatus), cassava (Manihot esculenta), coffee (Coffea spp.), coconut (Cocos nucifera), pineapple (Ananas comosus), citrus trees (Citrus spp.), cocoa (Theobroma cacao), tea (Camellia sinensis), banana (Musa spp.), avocado (Persea americana), fig (Ficus casica), guava (Psidium guajava), mango (Mangifera indica), olive (Olea europaea), papaya (Carica papaya), cashew (Anacardium occidentale), macadamia (Macadamia integrifolia), almond (Prunus amygdalus), sugar beets (Beta vulgaris), sugarcane (Saccharum spp.), oats, barley, vegetables, ornamentals, and conifers.

Vegetables include tomatoes (Lycopersicon esculentum), lettuce (e.g., Lactuca sativa), green beans (Phaseolus vulgaris), lima beans (Phaseolus limensis), peas (Lathyrus spp.), and members of the genus Cucumis such as cucumber (C. sativus), cantaloupe (C. cantalupensis), and musk melon (C. melo). Ornamentals include azalea (Rhododendron spp.), hydrangea (Macrophylla hydrangea), hibiscus (Hibiscus rosasanensis), roses (Rosa spp.), tulips (Tulipa spp.), daffodils (Narcissus spp.), petunias (Petunia hybrida), carnation (Dianthus caryophyllus), poinsettia (Euphorbia pulcherrima), and chrysanthemum.

Conifers that may be employed in practicing the present invention include, for example, pines such as loblolly pine (Pinus taeda), slash pine (Pinus elliotii), ponderosa pine (Pinus ponderosa), lodgepole pine (Pinus contorta), and Monterey pine (Pinus radiata); Douglas fir (Pseudotsuga menziesii); Western hemlock (Tsuga canadensis); Sitka spruce (Picea glauca); redwood (Sequoia sempervirens); true firs such as silver fir (Abies amabilis) and balsam fir (Abies balsamea); and cedars such as Western red cedar (Thuja plicata) and Alaska yellow-cedar (Chamaecyparis nootkatensis).

Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

The MSH2 promoter sequences of the invention can be used in methods for regulating gene expression in a plant. The methods of the invention involve operably linking an MSH2 promoter sequence of the invention to a second sequence wherein the MSH2 promoter allows the transcription of the second sequence. While the invention does not depend on a particular second sequence, preferred sequences are coding sequences. Such preferred sequences can additionally comprise 3' and 5' untranslated regions associated with the coding sequence. Such preferred sequences can be operably linked in either the sense or antisense orientation depending on the desired outcome.

The MSH2 promoter nucleotide sequences and methods disclosed herein are useful in regulating expression of any heterologous nucleotide sequence in a host plant in order to vary the phenotype of a plant. The methods of the invention involve operably linking an MSH2 promoter nucleotide sequence of the invention to heterologous nucleotide sequence wherein the MSH2 promoter allows the transcription of the heterologous nucleotide sequence.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997; and U.S. Pat. Nos. 5,703,049, 5,885,801, and 5,885,802, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) Eur. J. Biochem. 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) Proceedings of the World Congress on Vegetable Protein Utilization in Human Foods and Animal Feedstuffs, ed. Applewhite (American Oil Chemists Society, Champaign, Ill.), pp. 497–502; herein incorporated by reference); corn (Pedersen et al. (1986) J. Biol. Chem. 261:6279; Kirihara et al. (1988) Gene 71:359; both of which are herein incorporated by reference); and rice (Musumura et al. (1989) Plant Mol. Biol. 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, Bacillus thuringiensis toxic protein genes (U.S. Pat. Nos. 5,366,892; 5,747,450; 5,736,514; 5,723,756; 5,593,881; and Geiser et al. (1986) Gene 48:109); lectins (Van Damme et al. (1994) Plant Mol. Biol. 24:825); and the like.

Genes encoding disease resistance traits include detoxification genes, such as against fumonosin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. Modified hordothionin proteins are described in U.S. Pat. Nos.: 5, 990,389; 5,703,049; 5,885,801; and 5,885,802.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) J. Bacteriol. 170:5837–5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The invention further provides host cells transformed with at least one of the MSH2 nucleotide sequences of the invention. The host cells of the invention can be from any organism including, but not limited to, bacteria, fungi, animals and plants. A nucleotide construct comprising an MSH2 nucleotide sequence of the invention can be introduced into a host cell by any transformation methods known in the art. Such an introduced nucleotide construct can be stably integrated in the genome of the host cell or be present within the host cell in non-integrated form such as, for example, a plasmid, a cosmid, an artificial chromosome, or other vector. Expression cassettes can be constructed which include the nucleotide constructs of interest operably linked with the transcriptional and translational regulatory signals for expression of the nucleotide construct within the desired host cell.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523; 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

The host cells of the invention can be used as a source of MSH2 proteins for the isolation or purification of such proteins. If desired and using methods known to those of ordinary skill in the art, expression systems can be designed in such a manner to cause the MSH2 proteins to be secreted outside the cytoplasm of a bacterium, such as, for example, the gram-negative bacterium, *E. coli*. Advantages of having MSH2 secreted include, but are not limited to, (1) a reduction in, or avoidance of, potential cytotoxic effects of MSH2, and (2) an improvement in the efficiency of purification of MSH2. By "improvement in the efficiency of purification" is intended an improvement in at least one aspect of protein purification, including by not limited to, decreased cost of purification of a unit amount of protein, increased recovery of protein per purification attempt, increased recovery of active protein per purification attempt, and increased protein yield per bacterial cell or volume of culture broth. In addition, the invention encompasses fusion proteins comprising an MSH2 of the invention and a epitope or tag that can be used to facilitate purification and/or detection of such a fusion protein. Such epitopes or tags, and methods of use, are known in the art and include, for example, the polyhistidine-tag (his-tag).

MSH2 can be modified for secretion in *E. coli* by, for example, fusing an appropriate *E. coli* signal peptide to the amino-terminal end of the MSH2 protein. Signal peptides recognized by *E. coli* can be found in proteins already known to be secreted in *E. coli*, such as, for example the OmpA protein (J. Ghrayeb et al (1984) *EMBO J,* 3:2437–2442). OmpA is a major protein of the *E. coli* outer membrane and thus its signal peptide is thought to be efficient in the translocation process. Also, the OmpA signal peptide does not need to be modified before processing as may be necessary for other signal peptides, such as, for example the lipoprotein signal peptide (G. Duffaud et al. (1987) *Methods in Enzymology* 153:492).

The following examples are presented by way of illustration, not by way of limitation.

EXPERIMENTAL

Example 1

Isolation of an MSH2 cDNA from Tobacco

Materials and Methods

RNA extraction and RT-PCR. Total RNA was isolated by the LiCl method. Briefly, the method involves extraction of a tissue sample in 0.2 M NaOAC pH 5.2, 1% SDS, 0.5 mM EDTA pH 8.0. The resulting tissue slurry is extracted sequentially in phenol, phenol:chloroform (50:50), and chloroform. The resulting aqueous phase is precipitated in 2.5 M LiCl overnight at 4° C. Two to five µg of total RNA was reverse transcribed at 42° C. using 200 units MMLV reverse transcriptase (Promega, Madison, Wis.) in the buffer supplied, supplemented with 10 mM DTT and 1 mM dNTPs, in a 25 µL total volume.

Degenerate RT-PCR. Degenerate oligonucleotides were designed against highly conserved MutS family signature amino acid motifs; TGPNM (SEQ ID NO:22) and FATHY (SEQ ID NO:23) (Reenan and Kolodner (1992) *Genetics* 132:963–973). A typical PCR utilized 5 µL of a cDNA synthesis reaction (described above). PCR conditions consisted of 30–35 cycles of 96° C. for 13 sec., 48° C. for 45 sec. and 72° C. for 30 sec. Aliquots of the PCR products were ligated into pGemT-Easy (Promega) without purification. Putative tobacco MSH2 subclones were sequenced or tested for hybridization to heterologous DNA probes. Several identical tobacco MSH2 clones were identified by cross hybridization to an *Arabidopsis thaliana* var. Columbia genomic PCR product (Culligan and Hays (1997) *Plant Physiol.* 115:833–839) (Accession No. AF003005). The heterologous *Arabidopsis* probe was amplified from *Arabidopsis* genomic DNA using two oligonucleotides designated as AT-TG (5' GTAACAGGGCCTAACATGGG 3') (SEQ ID NO:24) and AT-FATH (5' GGAAGTGAGTAGCAAACAG 3')(SEQ ID NO:25). This resulting probe contains sequences encoding the Msh family signature region, as well as three introns (bases X–Y). Cloned PCR products were sequenced using Sequenase 2.0 (Amersham), or on an ABI 377 automated sequencer.

3' RACE

Five µg total RNA was reverse transcribed according to the Ready-2-go cDNA synthesis kit (Pharmacia). The PCR employed a gene-specific oligo "TG internal" (5' CAGGC-CCTAACATGGGTGG 3') (SEQ ID NO:26), in conjunction with the modified oligo dT included in the kit. Eleven µL of the 33 µL cDNA synthesis reaction was used for PCR according the manufacturer's instructions, except that the PCR was supplemented with 1 µL 5 mM dNTPs. Typical PCR conditions consisted of 35 cycles of 96° C. for 13 sec., 55° C. for 40 sec., 72° C. for 1.5 min. Aliquots of the PCR products were ligated into pGemT-Easy without purification. Plasmid clones were sequenced on an ABI 377 automated sequencer.

Generation of a full-length tobacco MSH2 cDNA. The tobacco MSH2 sequence was completed using a combination of 5' RACE, RT-PCR and inverse PCR (IPCR). Several upstream oligonucleotides were designed against amino acid motifs common to the *Arabidopsis thaliana* and *Saccharomyces cerevisiae* MSH2 proteins. These motifs included Y, MWLKQP (SEO ID NO:34), E. The sequences of upstream oligonucleotides against these putatively conserved amino acid motifs were identical to the known *A. thaliana* cDNA sequence (Culligan and Hays (1997) *Plant Physiol.* 115:833–839). In each RT-PCR, an oligonucleotide designed to hybridize to the known tobacco MSH2 sequence was used for the reverse transcription, and a nested oligonucleotide was used in conjunction with an upstream oligonucleotide for PCR. 5' RACE conditions followed the strategy of the Cap Finder 5' RACE kit (BRL). In short, purified reverse transcribed cDNA was 3' dC-tailed with terminal transferase (Promega) and dCTP. PCR of dC-tailed cDNA employed gene specific oligonucleotides and the G-anchor oligonucleotide (seq), using a cycling profile of 96° C. for 13 sec., 55–60° C. for 40 sec., 72° for 45 sec. IPCR was conducted on tobacco Nt-1 cell DNA digested with Xba I and recircularized by ligation, as reported elsewhere (Ochman et al. (19880 Genetics 149:641–650). Recircularized genomic DNA was amplified with two oligonucleotides; IPCR3 (5' AATGAAATGCAAGATTCTCC 3') (SEQ ID NO:27) and IPCR4 (5' GAAGCTTGCTCTGTTCCTCC 3') (SEQ ID NO:28). PCR products were cloned by ligation into pGemT-Easy. Plasmid clones were sequenced on an ABI 310 automated sequencer, using the Big Dye Terminator kit (Perkin-Elmer, Conn.).

DNA blot hybridizations. Plasmid clones (or PCR products) were transferred from agarose gels to Nytran Plus membranes using a vacuum blotter. The DNA was transferred from the gel for 1 hour in 0.4 M NaOH, and UV crosslinked to the membrane. Plasmid blots were hybridized for 2–5 hours at 65° C., using $^{32}$P-labelled, random-primed probes (Amersham) and washed twice in 40 mM NaPi (pH 7.2), 1 mM EDTA (pH 8) and 1% SDS. Radioactive signals were detected using a Phosphorimager (Molecular Dynamics, Sunnyvale, Calif.).

Genomic DNA was isolated from Nt-1 cells by the CTAB method and treated with pronase (Sambrook et al. (1989) Molecular Cloning: A Laboratory Manual, 2d ed., Cold Spring Harbor Laboratory Press, Plainview, N.Y.). Approximately 15 μg of tobacco DNA was restriction digested overnight at 37° C. in a 600 μL volume. Digestion products were precipitated with isopropanol and electrophoresed on a 0.7% agarose gel for 12 hrs. The gel was transferred to a Nytran Plus membrane by capillary blot in 12×SSC (Sambrook et al. (1989) Molecular Cloning: A Laboratory Manual, 2d ed., Cold Spring Harbor Laboratory Press, Plainview, N.Y.). The UV crosslinked membranes were hybridized to $^{32}$P-labelled (NEN-DuPont) random primed probes at >10$^9$ counts/mL, in a hybridization volume of 1–2 mL, for 14–18 hours. Radioactive signals were detected using a PhosphorImager or by exposure to film at −80° C. with an intensifying screen for 3–5 days.

Results

Degenerate oligonucleotides were designed against two highly conserved MutS family signature amino acid motifs; TGPNM (SEQ ID NO:22) (5' ACNGGNCCNAAYATGGG 3') (SEQ ID NO:29) and FATHY (SEQ ID NO:23) (5' TGYAARTGNGTNCGRAA 3') (SEQ ID NO:30) (Reenan and Kolodner (1992) Genetics 132:963–973). Degenerate RT-PCR product subclones were screened by hybridization to an A. thaliana probe, comprising the corresponding region of the A. thaliana MSH2 gene. Three candidate subclones were identified by southern analysis. The amplified sequence was highly homologous to the A. thaliana MSH2, and more similar to MSH2s than other Msh genes. A gene-specific oligonucleotide against the ATP binding site (5' CAGGCCCTAACATGGGTGG 3') (SEQ ID NO:31) was designed for 3' RACE. A 1.032 kb 3' RACE product was identified by hybridization to the previously identified sequences, which comprised the 3' end of the MSH2 coding region, as well as the 3' UTR. Additional 5' MSH2 cDNA sequences were obtained in a manner analogous to a chromosome walk utilizing degenerate RT-PCR and 5' RACE.

Two 5' degenerate oligonuclotides were designed to correspond to nucleotide sequences encoding the amino acid motifs DYYTAH (SEQ ID NO:32) (5' GATTATTATA-CAGCTCATGG 3') (SEQ ID NO:33) and MWLKQP (SEQ ID NO:34) (5'□ ATGTGGCTGAAACAACC 3') (SEQ ID NO:35), which are shared among the human, yeast and Arabidopsis MSH2 proteins. Whenever practical, an oligonucleotide designed to hybridize to the known tobacco MSH2 sequence was used for the reverse transcription and a nested oligonucleotide was used in conjunction with an upstream oligonucleotide for PCR. A typical PCR utilized 5 mL of a cDNA synthesis reaction, and followed the reaction condition parameters described above. The 3' oligonucleotides ultilized for degenerate RT-PCR of the "M" product (to be used in conjunction with SEQ ID NO:34) were designated as the "unique R1" primer(5' CTTATGTCCAT-TGTCTCCATTC 3' (SEQ ID NO:36) for cDNA syntesis) and the "unique R2" nested primer (5' GTCCATTGTCTC-CATTCTTG 3', (SEQ ID NO:37) for PCR of cDNA). The 3' oligonucleotides for degenerate RT-PCR of the "D" product (used in conjunction with the 5' DYYTAH oligonucleotide (SEQ ID NO:33) were designated as the "22a" primer (5' GCACCCCAAAGCGCCTGATG 3' (SEQ ID NO:38), for cDNA synthesis) and the "22b" nested primer (5' CTGAT-GCACATTCGAACCCAGAG 3' (SEQ ID NO:39), for PCR of cDNA). PCR conditions were 96° C. for 17 s, 48–55° C. for 45 s, 72° C. for 30 s to 2 min for each cycle, and with a total of 30–35 cycles conducted using a thermocycler (ABI 9700). The degenerate RT-PCR products (and/or their subdlones) were identified by hybridization to previously characterized, overlapping NtMSH2 sequences.

Sequence analysis of subcloned 5' RACE products generated from the 5' ends of the transcripts revealed several nucleotide polymorphisms within the coding region as well as the 5' untranslated regions (UTRs) of the MSH2 transcripts. Among the 5' UTR polymorphisms between the alleles is a homonucleotide run of either nine or eleven consecutive adenines. In each 5' UTR, the last base of the homoA run is the A of the start codon (ATG), leading to an atypical translation initiation context for the MSH2 mRNAs.

To further characterize nucleotide polymorphisms found in the 5' ends of the MSH2 transcripts, a 169 bp section of the MSH2 was amplified by RT-PCR and the products were subdloned and sequenced. The DNA sequence of these RT-PCR products fell into distinct groups based upon nucleotide polymorphisms at six sites (FIG. 1). This analysis revealed two different MSH2 proteins as the nucleotide polymorphism at cDNA position 145, T or G, leads to non-degenerate codons; TCT, encoding serine, or GCT, encoding alanine at amino acid position 49. Additionally, two polymorphic (degenerate) versions of the sequence containing the alanine codon were identified. The presence of two distinct protein coding regions and multiple polymorphic mRNAs was confirmed by sequencing PCR products amplified from tobacco genomic DNA as described below.

Approximately 15 μg of tobacco genomic DNA, derived from Nt-1 cells, was digested with the restriction enzymes Hind III, Sst I or Xba I and blotted to a nylon membrane using standard molecular biology methods (Sambrook et al. (1989) Molecular Cloning: A Laboratory Manual, 2d ed., Cold Spring Harbor Laboratory Press, Plainview, N.Y.). The hybridization pattern of the 5' MSH2 cDNA probe indicated the presence of two similar MSH2 loci (data not shown). The probe hybridized to two species in lane 1 (Hind III) and two similar sized species in lane 3 (Xba I). A 3' MSH2 cDNA probe (panel b), which contains the Msh family signature sequences, hybridizes to a large number of bands, suggesting hybridization to other members of an as yet unidentified Msh gene family.

Example 2

Identification of MSH2 Regulatory Elements and Demonstration of MSH2 Promoter Activity By comparing the restriction map generated from the tobacco MSH2 cDNA sequence and the data from the genomic Southern blots, it was expected that the approximately 1.7 kb XbaI fragments identified by the Southern analysis (Example 1) should contain a substantial portion of the 5' end of the genes. Inverse PCR (IPCR) was utilized to amplify flanking MSH2 sequences (SEQ ID NOS:5–12). Oligonucleotides were designed to hybridize just 3' of the start codon and approximately 100 bases 5' of the first XbaI site identified in the cDNA sequence. IPCR amplified two distinct promoter-like sequences, designated class I and class II, as well as the adjacent 5' UTR sequences. The sequences of these regulatory elements are polymorphic at several sites, summarized in (SEQ ID NOS:5–12). Notably, the class I promoter element contains a canonical CCAAT box; the corresponding sequence of the class II element is CCAAC. Additionally, the class I MSH2 promoter contains a ten base insertion that is completely absent in the class II element. This ten base insertion is nearly a perfect direct repeat, consistent with a role in DNA:protein interaction. Each class of MSH2 promoter has an identical TATA element. Nucleotide polymorphisms previously identified within the distinct 5' UTRs were confirmed, and two additional SNPs (single nucleotide polymorphisms) were found in sequences between the TATA element and the start codon. These could not be definitively ascribed to the promoter or the coding region, as efforts to conduct primer extension were unsuccessful.

Each MSH2 regulatory element was fused to a uidA reporter and bombarded into lawns of Nt-1 cells. Bombarded cells were assayed for accumulation of GUS protein by histochemical assay and for the transcription of MSH2:uidA mRNA by RT-PCR (data not shown). GUS staining in the bombarded cells and RT-PCR analysis demonstrated that each promoter element is competent to transcribe mRNA (data not shown).

Example 3

Amplification and Sequencing of Genomic DNAs Corresponding to the 5' Ends of the MSH2 Alleles To establish which promoter sequences drive the polymorphic mRNAs, oligonucleotides were designed to amplify regions between the promoters and nucleotide 179 of the cDNA sequence. Genomic PCR products were ligated into pGem-T Easy (Promega Corp., Madison, Wis.), and the resulting plasmid subdlones were sequenced. Genomic PCR products representing the two promoter classes as well as each of the three classes of polymorphic mRNA (SEQ ID NOS:13–15) were identified through DNA sequencing. Each product also contained three introns, which are present at the same location in the cDNA sequence with respect to the start codon, but exhibit varying levels of polymorphism when compared to one another. When the promoters (SEQ ID NOS:5–12), 5' UTRs (SEQ ID NOS:13–15), coding regions (SEQ ID NOS:1 and 3) and introns (SEQ ID NOS:16–21) were compared, it was determined that four distinct MSH2 genes had been identified. Three of the genes have a class II promoter, while only one gene bearing a class I promoter was identified. The transcript linked to the class I promoter encodes serine at amino acid 49, and has the G/C rich set of SNPs. Three distinct genes with class II promoters were identified. One gene contains the G/C rich set of SNPs, and encodes serine at amino acid 49. The other two genes have the A/T rich set of SNPs, but they differ by a two nucleotide base polymorphism resulting in either an alanine or serine codon at position 49. In addition to the two base polymorphism, there are substantial differences between the introns of these two genes with the A/T rich SNPs set. For example, the second intron of the gene encoding alanine (107 nucleotides in length) and the second intron of the gene encoding serine (105 nucleotides) differ by two insertion/deletions and eight SNPs.

Example 4

MSH2 Expression Levels and Distribution

Materials and Methods

Antibody production and immunoblotting. The $(His)_6$ vector pQE31 (Qiagen; Valencia, Calif.) was restricted with BamHI and filled with the Klenow large fragment (Sambrook et al. (1989) Molecular Cloning: A Laboratory Manual, 2d ed., Cold Spring Harbor Laboratory Press, Plainview, N.Y.) to create a blunt end, then digested with Hind III (NEB). A restriction fragment of the tobacco cDNA sequence, spanning the codons for amino acids 670–939 was ligated into the prepared vector as a Klenow filled Sal I/Hind III fragment to generate the $(His)_6C$ fusion protein.

The $(His)_6C$ fusion protein was purified using the NTA-nickel matrix under denaturing conditions following the manufacturer's recommendations (Qiagen, Valencia, Calif.). The purified protein was dialyzed against PBS (phosphate-buffered saline), in the presence of 10 mM 2-mercaptoethanol and 0.3 mM PMSF. The dialyzed protein was concentrated threefold using a Centricon spin concentrator, according to the manufacturers instructions (Amicon). Rabbit antisera was produced by the Cornell Veterinary School using the purified protein.

Total proteins were extracted from frozen pulverized tobacco tissues in 20 mM Na phosphate (pH 6.6), 100 mM NaCl, 1 mM EDTA pH 8, 0.1 mM β-mercaptoethanol, 0.5 mM PMSF and 15 mg/L leupeptin. Thirty-five µg samples of protein isolated separately from tobacco Nt-1 cells and from tobacco leaf, root, and flower tissues were electrophoresed through 8% polyacrylamide gels and transferred to Transblot nitrocellulose membranes (BioRad) using a Transblot apparatus (BioRad), according to the manufacturer's instructions. Rabbit anti-tMSH2 immune serum was incubated with membranes at a 1–900 dilution for 3 hours at 25° C. in TBS (Tris-buffered saline) (Sambrook et al. (1989) Molecular Cloning: A Laboratory Manual, 2d ed., Cold Spring Harbor Laboratory Press, Plainview, N.Y.) with 5% dry milk and 0.05% $NaN_3$. The primary antibody was detected using an anti-rabbit HRP-conjugated secondary antibody (Sigma).

Relative RT-PCR. Three independently isolated five µg samples of total RNA were prepared from flower, leaf and root tissues and then reverse transcribed at 42° C. as described above following RQ-DNAse treatment (Promega Corp., Madison, Wis.). A linear range of amplification was determined for each tissue (data not shown). Individual PCR reactions were conducted using 1 µL of each of the 25 µL cDNA syntheses, for 22, 24, 26 and 28 cycles. The cDNA synthesis employed the 3' RtB primer (5' ACATATAGT-TCAAGAGTACGGT 3') (SEQ ID NO:40). The resulting cDNA products were re-amplified with the 3' RtA primer (3' GCTATTGTTTCAAACATGTTTC 3') (SEQ ID NO:41) and the 5'MSH primer (5' TTGGAGGAACAGAG-CAAGCTTC 3') (SEQ ID NO:42). Amplification products were electrophoresed and quantitated by measuring ethidium bromide fluorescence (Eagle Eye, Stratagene).

Ethidium bromide band intensities were plotted vs. cycle number for each tissue type, and linear ranges were established. To compare the samples from each tissue, a 1 µL volume of each cDNA synthesis was PCR amplified for 25 cycles.

Results

The levels of MSH2 protein were assessed in mature leaf, callus derived from leaf, root, flower (total), anther/pollen, stigma/style, ova petal, sepal and Nt-1 cells. Total protein was measured by the method of Bradford. Results from the immunoblotting of approximately 35 µg total protein samples indicated the presence of MSH2 in all tobacco tissues tested. As a control to demonstrate the integrity of the protein samples, the membranes were also incubated with antisera against ascorbate reductase. The accumulation of MSH2 varies substantially between tissues, and consistently accumulates to relatively higher levels in actively dividing tissues (data not shown). Several interesting trends were observed. The MSH2 protein seems to accumulate to higher levels in female gametophytic tissues compared to male gametophytic tissues (data not shown). Finally, Nt-1 cells, the most actively dividing tissue of those tested, had a large accumulation of MSH2 protein. These data suggest that MSH2 protein accumulates in actively dividing cells, but is still present in non-dividing cells.

The accumulation of MSH2 mRNA was measured utilizing the Invader Assay Invader Assay (Third Wave Technologies). (Lyamichev et al. (1998) *Nature Biotech.* 17:292–296).

Example 5

Expression of the MSH2 N-terminal Region Confers a Mutator Phenotype

Materials and Methods

Dominant negative overexpression of a tobacco MSH2 sequence in *E. coli*. The $(His)_6$ vector pQE30 (Qiagen; Valencia, Calif.) was restricted with Hind III and filled with the Klenow large fragment (Sambrook et al. (1989) Molecular Cloning: A Laboratory Manual, 2d ed., Cold Spring Harbor Laboratory Press, Plainview, N.Y.) to create a blunt end, then digested with BamH I. An RT-PCR product of the tMSH2 sequence was created using the 22-base oligonucleotide and an oligonucleotide overlapping the tMSH2 start codon which generated a unique BamH I restriction enzyme site just upstream of the ATG. This RT-PCR product was ligated into pGem-T Easy. The resulting plasmid was digested with EcoR I, blunted with Klenow, and subsequently BamH I digested. This blunt-EcoR I fragment encoding the first 265 amino acids of the tobacco MSH2 protein was ligated into the BamH I/blunt pQE30 described above to create $(His)_6N$. Fragments encoding the $(His)_6$-MSH2 fusions ($(His)_6C$ and $(His)_6N$) were sequenced on an ABI 310 automated sequencer.

*E. coli* cells (XL-1 blue, Stratagene) harboring pQE-MSH2 fusions or pKSII (Stratagene) were grown for 6 hours in LB media containing 100 µg/mL ampicillin and 0.05 mM IPTG to induce production of the protein fusions or the α-peptide of β-galactosidase. Cell culture dilutions were plated onto LB plates containing 100 µg/mL ampicillin to determine cell viability. Mutated cells were selected on plates containing 100 µg/mL ampicillin and 150 µg/nL rifampicin (Reenan and Kolodner (1992) *Genetics* 132:963–973).

Results

The overexpression of a MutS homolog in an heterologous system can lead to a dominant mutator phenotype. To determine if the tobacco MSH2 could cause a mutator phenotype in *E. coli*, an $(His)_6$-tagged, IPTG-inducible plasmid clone (Qiagen, Valencia, Calif.) was constructed by cloning the nucleotides 1–797 of SEQ ID NO: 1, which encodes the N-terminal 265 amino acids of the tobacco MSH2 ($(His)_6N$) into pQE30 (Qiagen, Valencia, Calif.). The N-terminus of MutS has been shown to interact directly with DNA (Malkov et al. (1997) *J. Biol. Chem.* 272: 23811–23817) via a DYYT (amino acid positions 1–4 of SEQ ID NO:32) motif. This amino acid motif is present in all identified MSH2 proteins, including the tobacco homologue. Parallel fluctuation analysis was performed on 11 independent XL-1 blue (Stratagene, La Jolla Calif.) cultures containing either pBluescriptKS or $(His)_6N$ plasmids. Mutation rates were determined by plating cells on LB plates containing 150 mg/L rifampicin and 100 mg/L ampicillin after 6 hrs. growth in 5 µM IPTG. The total number of viable cells in each culture was estimated by counting ampicillin-resistant colonies from dilutions of the cell cultures.

Example 6

The Tobacco MSH2 Exists in Higher Molecular Weight Complexes

Nuclear extracts derived from tobacco NT-1 cells were subjected to density centrifugation in sucrose gradients. Seventeen fractions from 4–19% sucrose gradients were collected, and gradient fractions containing MSH2 were identified by SDS-PAGE followed by immunoblotting. Parallel sucrose gradients containing marker proteins of known molecular weight (*E. coli* alkaline phosphatase (80 kDa), α-amylase (220 kDa), and apoferitin (450 kDa)) were used to approximate the molecular weight range of fractions containing MSH2. Immunoblotting of gradient fractions revealed that MSH2 could be detected in disparate regions of the gradients, in fractions 3 and 4 (approximately 80 kDa) and also in fraction 9 (approximately 260 kDa).

Example 7

Transformation and Regeneration of Transgenic Maize Plants

Immature maize embryos from greenhouse donor plants are bombarded with a plasmid containing an MSH2 operably linked to a maize ubiquitin plus a plasmid containing the selectable marker gene PAT (Wohlleben et al. (1988) *Gene* 70:25–37) that confers resistance to the herbicide Bialaphos. Transformation is performed as follows. Media recipes follow below.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Bombardment and Culture Media

Bombardment medium (560Y) comprises 4.0 g/l N6 basal salts (SIGMA C-1416), 1.0 ml/L Eriksson's Vitamin Mix (1000X SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 ml/L Eriksson's Vitamin Mix (1000X SIGMA- 1511), 0.5 mg/L thiamine HCl, 30.0 g/L sucrose, and 2.0 mg/L 2,4-D (brought to volume with D-I H$_2$0 following adjustment to pH 5.8 with KOH); 3.0 g/L Gelrite (added after bringing to volume with D-I H$_2$O); and 0.85 mg/L silver nitrate and 3.0 mg/L bialaphos(both added after sterilizing the medium and cooling to room temperature).

Plant regeneration medium (288J) comprises 4.3 g/L MS salts (GIBCO 11117–074), 5.0 ml/L MS vitamins stock solution (0.100 g nicotinic acid, 0.02 g/L thiamine HCl, 0.10 g/l pyridoxine HCL, and 0.40 g/L glycine brought to volume with distilled D-I H$_2$O) (Murashige and Skoog (1962) Physiol. Plant. 15:473), 100 mg/l myo-inositol, 0.5 mg/L zeatin, 60 g/L sucrose, and 1.0 ml/L of 0.1 mM abscisic acid (brought to volume with polished D-I H$_2$O after adjusting to pH 5.6); 3.0 g/L Gelrite (added after bringing to volume with D-I H$_2$O); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117–074), 5.0 ml/L MS vitamins stock solution (0.100 g/L nicotinic acid, 0.02 g/L thiamine HCl, 0.10 g/L pyridoxine HCl, and 0.40 g/L glycine brought to volume with polished D-I H$_2$O), 0.1 g/L myo-inositol, and 40.0 g/L sucrose (brought to volume with polished D-I H$_2$O after adjusting pH to 5.6); and 6 g/L bacto-agar (added after bringing to volume with polished D-I H$_2$O), sterilized and cooled to 60° C.

Preparation of DNA

A plasmid vector comprising the MSH2 operably linked to a maize ubiquitin is made. This plasmid DNA plus plasmid DNA containing a PAT selectable marker is precipitated onto 1.1 μm (average diameter) tungsten pellets using a CaCl$_2$ precipitation procedure as follows:

100 μL prepared tungsten particles in water
10 μL (1 μg) DNA in TrisEDTA buffer (1 μg total)
100 μL 2.5 M CaCl$_2$
10 μL 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for MSH2 biological activity.

Example 8

Agrobacterium-mediated Transformation and Regeneration of Transgenic Maize Plants For Agrobacterium-mediated transformation of maize with an MSH2 nucleotide sequence of the invention, preferably the method of Zhao is employed (PCT patent publication WO98/32326), the contents of which are hereby incorporated by reference. Briefly, immature embryos are isolated from maize and the embryos contacted with a suspension of Agrobacterium, where the bacteria are capable of transferring the MSH2 nucleotide sequence of interest to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 9

Production of Transgenic Soybean Plants Using Embryo Transformation

Soybean embryos are bombarded with a plasmid containing MSH2 nucleotide sequence of the invention operably linked to a SCP1 or UCP3 promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the MSH2 nucleotide sequence of the invention operably linked to the SCP1 or UCP3 promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a micro fuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 10

Production of Transgenic Sunflower Plants Using Meristem Tissue Transformation

Sunflower meristem tissues are transformed with an expression cassette containing an MSH2 nucleotide sequence of the invention operably linked to a SCP1 promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) *Plant Mol. Biol.* 18: 301–313). Thirty to forty explants are placed in a circle at the center of a 60×20 mm plate for this treatment. Approximately 4.7 mg of 1.8 μm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the MSH2 nucleotide sequence of the invention operably linked to the SCP1 promoter is introduced into *Agrobacterium* strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l NH4Cl, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for MSH2 activity. See, Su et al. ((1988) *J. Biol. Chem.* 263:6829–6835), Holmes et al. ((1990) *Proc. Natl. Acad. Sci. USA* 87:5837–5841), and Rice et al. ((2000) *Plant Physiol.* 123:427–438).

NPTII-positive shoots are grafted to Pioneer® hybrid 6440 in vitro-grown sunflower seedling rootstock. Surface sterilized seeds are germinated in 48–0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with Parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by MSH2 activity analysis of leaf extracts while transgenic seeds harvested from NPTII-positive $T_0$ plants are identified by MSH2 activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 $\mu$m tungsten particles are resuspended in 150 $\mu$l absolute ethanol. After sonication, 8 $\mu$l of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 $\mu$g/l kanamycin is resuspended in an inoculation medium (12.5 mM 2-(N-morpholino) ethanesulfonic acid, MES, 1 g/l NH$_4$Cl and 0.3 g/l MgSO$_4$ at pH 5.7) to reach a final OD6$_{00}$ of 4.0. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 $\mu$g/ml cefotaxime). The plantlets are cultured on the medium for about two weeks under 16-hour day and 26° C. incubation conditions.

Explants (around 2 cm long) from two weeks of culture in 374C medium are screened for expression of the selectable marker gene and then those that are positive for expression of the marker gene are then screened for MSH2 activity using assays known in the art. After positive (i.e., for MSH2 expression) explants are identified, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for MSH2 expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

We claim:

1. An isolated nucleic acid molecule comprising a nucleotide sequence selected from the group consisting of:

(a) the nucleotide sequence set forth in SEQ ID NO: 1 or 3;

(b) a nucleotide sequence encoding the amino acid sequence set forth in SEQ ID NO: 2 or 4;

(c) a nucleotide sequence encoding residues 1–265 of the amino acid sequence set forth in SEQ ID NO: 2 or 4;

(d) an antisense nucleotide sequence corresponding to the nucleotide sequence of (a), (b) or (c);

(e) a nucleotide sequence encoding a fragment or variant of the amino acid sequence set forth in SEQ ID NO: 2 or 4, wherein said fragment or said variant confers a dominant-negative phenotype in a host cell and said variant has at least 95% sequence identity to at least one amino acid sequence selected from the group consisting of the amino acid sequences set forth in SEQ ID NOS: 2 and 4[, and wherein percent sequence identify is obtained using GAP version 10 with a GAP Weight of 50 and a Length Weight of 3];

(f) a nucleotide sequence encoding an amino acid sequence having at least 95% sequence identify to at least one amino acid sequence selected from the group consisting of the amino acid sequences set forth in SEQ ID NOS: 2 and 4, wherein said nucleotide sequence encodes a protein comprising mismatch-repair; and (g) nucleotides 1–797 of SEQ ID NO: 1.

2. An expression cassette comprising a promoter operably linked to the nucleic acid molecule of claim 1.

3. The expression cassette of claim 2, wherein said promoter drives expression in a plant.

4. The expression cassette of claim 3, wherein said promoter is selected from the group consisting of constitutive, pathogen-inducible, insect-inducible, wound-inducible, tissue-preferred, and developmentally regulated promoters.

5. A transformed plant comprising in its genome at least one stably incorporated nucleotide construct comprising a promoter that drives expression in a plant operably linked to the nucleic acid molecule of claim 1.

6. The plant of claim 5, wherein said promoter is selected from the group consisting of constitutive, tissue-preferred and developmentally regulated promoters.

7. The plant of claim 5, wherein said plant is a monocot.

8. The plant of claim 7, wherein said monocot is selected from the group consisting of maize, wheat, rice, sorghum, barley, millet and rye.

9. The plant of claim 5, wherein said plant is a dicot.

10. The plant of claim 9, wherein said dicot is selected from the group consisting of tobacco, tomato, potato, soybean, *Brassica sp.*, alfalfa, safflower, sunflower, cotton, and peanut.

11. Transformed seed of the plant of claim 5.

12. A transformed plant cell comprising in its genome at least one stably incorporated nucleotide construct comprising a promoter that drives expression in a plant cell operably linked to the nucleic acid molecule of claim 1.

13. A method for altering recombination frequency in a plant comprising introducing into a plant the nucleic acid molecule of claim 1, wherein said recombination frequency is increased or decreased in said plant or at least one cell thereof.

14. The method of claim 13, wherein said nucleic acid molecule is operably linked to a promoter that drives expression in a plant cell.

15. The method of claim 14, wherein said promoter is operably linked to said nucleic acid molecule for the production of antisense transcripts.

16. The method of claim 14, wherein said promoter is selected from the group consisting of constitutive, tissue-preferred and developmentally regulated promoters.

17. The method of claim 13, wherein said plant or at least one cell thereof comprises a dominant negative phenotype.

18. The method of claim 13, wherein efficiency of chimeraplasty is increased in said plant or at least one cell thereof.

19. A method for altering DNA repair processes in a plant comprising introducing into a plant a nucleotide sequence selected from the group consisting of:

(a) the nucleotide sequence set forth in SEQ ID NO: 1 or 3;

(b) a nucleotide sequence encoding the amino acid sequence set forth in SEQ ID NO: 2 or 4;

(c) a nucleotide sequence encoding residues 1–265 of the amino acid sequence set forth in SEQ ID NO: 2 or 4;

(d) an antisense nucleotide sequence corresponding to the nucleotide sequence of (a), (b) or (c);

(e) a nucleotide sequence encoding a fragment or variant of the amino acid sequence set forth in SEQ ID NO: 2 or 4, wherein said fragment or said variant confers a dominant-negative phenotype in a host cell and said variant has at least 95% sequence identify to at least one amino acid sequence selected from the group consisting of the amino acid sequences set forth in SEQ ID NOS: 2 and 4, (f) a nucleotide sequence encoding an amino acid sequence having at least 95% sequence identify to at least one amino acid sequence selected from the group consisting of the amino acid sequences set forth in SEQ ID NOS: 2 and 4, wherein said nucleotide sequence encodes a protein comprising mismatch-repair activity; and (g) nucleotides 1–797 of SEQ ID NO: 1.

20. The method of claim 19, wherein the efficiency of gene modification in said plant is increased.

21. The method of claim 20, wherein efficiency of chimeraplasty is increased in said plant.

22. The method of claim 19, wherein mismatch repair is altered in said plant.

23. The method of claim 19 further comprising operably linking to said nucleotide sequence a promoter that drives expression in a plant cell.

24. The method of claim 23, wherein said promoter is selected from the group consisting of constitutive, tissue-preferred and developmentally regulated promoters.

25. The method of claim 19 further comprising introducing a dominant negative mutation into said nucleotide sequence.

26. The method of claim 19, wherein said nucleic acid molecule confers a dominant negative phenotype on said plant or at least one cell thereof.

27. The method of claim 19 wherein efficiency of chimeraplasty is increased in said plant.

28. A non-human host cell comprising in its genome a nucleotide construct comprising the nucleic acid molecule of claim 1.

29. The host cell of claim 28, wherein said nucleotide construct further comprises an operably linked promoter that is capable of driving expression of said nucleic acid molecule in said host cell.

30. An isolated nucleic acid molecule comprising a nucleotide sequence encoding an amino acid sequence having at least 95% sequence identify to at least one amino acid sequence selected from the group consisting of the amino acid sequences set forth in SEQ ID NOS: 2 and 4, wherein said nucleotide sequence encodes a protein comprising mismatch-repair activity.

31. A transformed plant comprising in its genome at least one stably incorporated nucleotide construct comprising a promoter that drives expression in a plant operably linked to the nucleic acid molecule of claim 30.

* * * * *

UNITED STATES PATENT AND TRADEMARK OFFICE
CERTIFICATE OF CORRECTION

PATENT NO.      : 6,906,243 B2
DATED           : June 14, 2005
INVENTOR(S)     : Peter B. Kipp et al.

It is certified that error appears in the above-identified patent and that said Letters Patent is hereby corrected as shown below:

Column 75,
Lines 66-67, should read as follows:
-- (d) an antisense nucleotide sequence of the nucleotide sequence of (a), (b) or (c); --.

Column 77,
Lines 1-16, should read as follows:
-- (e) a nucleotide sequence encoding a fragment or variant of the amino acid sequence set forth in SEQ ID NO: 2 or 4, wherein said fragment or said variant confers a dominant-negative phenotype in a host cell and said variant has at lease 95% sequence identity to at least one amino acid sequence selected from the group consisting of the amino acid sequences set forth in SEQ ID NO: 2 and 4; --.
Lines 11-16, should read as follows:
-- (f) a nucleotide sequence encoding an amino acid sequence having at least 95% sequence identity to at least one amino acid sequence selected from the group consisting of the amino acid sequences set forth in SEQ ID NOS: 2 and 4, wherein said nucleotide sequence encodes a protein comprising mismatch-repair activity; and --.

Column 78,
Lines 8-9, should read as follows:
-- (d) an antisense nucleotide sequence of the nucleotide sequence of (a), (b) or (c); --.
Lines 11-18, should read as follows:
-- (e) a nucleotide sequence encoding a fragment or variant of the amino acid sequence set forth in SEQ ID NO: 2 or 4, wherein said fragment or said variant confers a dominant-negative phenotype in a host cell and said variant has at lease 95% sequence identity to at least one amino acid sequence selected from the group consisting of the amino acid sequences set forth in SEQ ID NO: 2 and 4; --.

UNITED STATES PATENT AND TRADEMARK OFFICE
CERTIFICATE OF CORRECTION

PATENT NO.    : 6,906,243 B2
DATED         : June 14, 2005
INVENTOR(S)   : Peter B. Kipp et al.

It is certified that error appears in the above-identified patent and that said Letters Patent is hereby corrected as shown below:

<u>Column 78 (cont'd)</u>,
Lines 19-25, should read as follows:
-- (f) a nucleotide sequence encoding an amino acid sequence having at least 95% sequence identity to at least one amino acid sequence selected from the group consisting of the amino acid sequences set forth in SEQ ID NOS: 2 and 4, wherein said nucleotide sequence encodes a protein comprising mismatch-repair activity; and --.

Signed and Sealed this

Eleventh Day of October, 2005

JON W. DUDAS
*Director of the United States Patent and Trademark Office*